United States Patent

Brand et al.

Patent Number: 5,395,854
Date of Patent: Mar. 7, 1995

[54] ORTHO-SUBSTITUTED PHENYLACETAMIDES

[75] Inventors: Siegbert Brand, Birkenheide; Eberhard Ammermann, Ludwigshafen; Gisela Lorenz, Neustadt; Hubert Sauter, Mannheim; Klaus Oberdorf, Eppelheim; Uwe Kardorff, Mannheim; Christoph Kuenast, Otterstadt, all of Germany

[73] Assignee: BASF Aktiengesellschaft, Ludwigshafen, Germany

[21] Appl. No.: 124,437

[22] Filed: Sep. 22, 1993

Related U.S. Application Data

[63] Continuation of Ser. No. 751,955, Aug. 29, 1991, abandoned.

[30] Foreign Application Priority Data

Sep. 22, 1990 [DE] Germany .............. 40 30 038.2

[51] Int. Cl.$^6$ .............. A01N 37/18; C07C 233/05
[52] U.S. Cl. .................. 514/619; 514/63; 514/269; 514/274; 514/312; 514/333; 514/335; 514/336; 514/338; 514/346; 514/367; 514/459; 514/461; 514/618; 544/229; 544/296; 544/316; 544/317; 546/14; 546/153; 546/157; 546/256; 546/261; 546/270; 546/283; 548/110; 548/157; 548/171; 549/214; 549/414; 549/415; 549/419; 549/473; 549/496; 564/162; 564/165; 564/167; 564/163; 564/164
[58] Field of Search .............. 564/165, 167, 163, 164, 564/167; 514/618, 620, 619

[56] References Cited

U.S. PATENT DOCUMENTS

| | | | |
|---|---|---|---|
| 4,415,743 | 11/1983 | Martin | 564/165 |
| 4,829,085 | 5/1989 | Wenderoth et al. | 514/522 |
| 4,952,720 | 8/1990 | Schuetz et al. | 560/106 |
| 5,051,447 | 9/1991 | Wenderoth et al. | 514/534 |
| 5,185,342 | 2/1993 | Hayase et al. | 514/274 |

FOREIGN PATENT DOCUMENTS

| | | |
|---|---|---|
| 0088325 | 9/1983 | European Pat. Off. |
| 0398692 | 11/1990 | European Pat. Off. |
| 280317 | 8/1978 | Germany . |
| 636601 | 6/1983 | Switzerland . |

Primary Examiner—Shailendra Kumar
Attorney, Agent, or Firm—Oblon, Spivak, McClelland, Maier & Neustadt

[57] ABSTRACT

Ortho-substituted phenyl-acetamides I

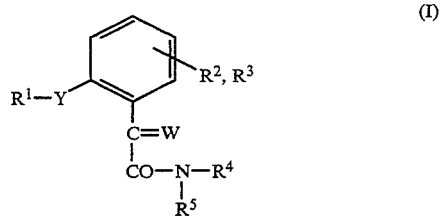

($R^1$=H, alkyl, cycloalkyl, alkenyl, alkynyl, phenylalkynyl, alkoxyalkyl, alkoxycarbonyl, phenyl, phenylalkyl, phenylalkenyl or phenoxyalkyl, 5- or 6-membered heterocycle with 1–3 hetero atoms to which a benzene ring or a 5- or 6-membered heterocycle can be fused; $R^2$ and $R^3$=H, CN, halogen, alkyl, alkoxy; $R_4$ and $R^5$=H, alkyl and $R^4$ or $R^5$=alkoxy; Y=O, S, SO, $SO_2$, N=N, O—CO, CO—O, CO—O—$CH_2$, alkylene or haloalkylene, alkenylene, alkynylene, oxy-alkylene, thio-alkylene, alkyleneoxy, carbonylalkylene or alkylenecarbonyl, W=alkoxyimino, alkoxymethylene or alkylthiomethylene), excepting compounds where $R^1$ is hydrogen, phenyl or 2,2-dimethyl-3-(2,2-dichlorovinyl)cyclopropyl, $R^2$ to $R^5$ are each hydrogen, Y is carbonyloxymethylene and W is methoxymethylene or methylthiomethylene, are suitable as fungicides and for controlling pests.

6 Claims, No Drawings

ORTHO-SUBSTITUTED PHENYLACETAMIDES

This application is a continuation of application Ser. No. 07/751,955, filed on Aug. 29, 1991, now abandoned.

The present invention relates to novel ortho-substituted phenylacetamides of the formula I

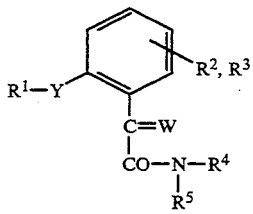

where
- $R^1$ is hydrogen, $C_1$–$C_{18}$-alkyl, $C_3$–$C_8$-cycloalkyl which can have from one to three substituents selected from a group of 3 halogen atoms, 3 $C_1$–$C_4$-alkyl groups, a partially or completely halogenated $C_1$–$C_4$-alkenyl group and a phenyl group which can carry one or two halogen atoms and/or one $C_1$–$C_4$-alkyl group and/or one $C_1$–$C_4$-alkoxy group, or is $C_2$–$C_{10}$-alkenyl, $C_2$–$C_4$-alkynyl which can carry a phenyl radical, or is $C_1$–$C_4$-alkoxy-$C_1$–$C_4$-alkyl, $C_1$–$C_4$-alkoxycarbonyl, phenyl, phenyl-$C_1$–$C_4$-alkyl or phenyl-$C_2$–$C_4$-alkenyl or phenoxy-$C_1$–$C_4$-alkyl where each aromatic ring can have from one to five substituents selected from a group of 2 nitro radicals, 2 cyano radicals, 5 halogen atoms and in each case three of the following: $C_1$–$C_4$-alkyl, partially or completely halogenated $C_1$–$C_4$-alkyl, $C_2$–$C_4$-alkenyl, partially or completely halogenated $C_2$–$C_4$-alkenyl and $C_1$–$C_4$-alkoxy, and of one phenyl, benzyl, phenoxy, benzyloxy or phenylthio radical, where the last two radicals in turn can have one or two of the following substituents: cyano, halogen or $C_1$–$C_4$-alkyl; a 5- or 6-membered heterocycle with from one to three hetero atoms selected from a group of two oxygen, two sulfur and three nitrogen atoms, excepting compounds with two adjacent oxygen and/or sulfur atoms, it being possible for a benzene ring or a 5- or 6-membered heteroaromatic ring with one nitrogen, oxygen or sulfur atom to be fused on to the heterocycle, and it being possible for the heterocycle to carry one halogen atom, one or two $C_1$–$C_4$-alkyl radicals or one phenyl radical;
- $R^2$ and $R^3$ are each, independently of one another, hydrogen, cyano, halogen, $C_1$–$C_4$-alkyl or $C_1$–$C_4$-alkoxy;
- $R^4$ and $R^5$ are each, independently of one another, hydrogen or $C_1$–$C_4$-alkyl or one of the two is $C_1$–$C_4$-alkoxy;
- Y is oxygen, sulfur, —SO—, —SO$_2$—, —CH$_2$—O—SO$_2$—, —N=N—, —O—CO—, —CO—O— or —CO—O—CH$_2$—, $C_1$–$C_4$-alkylene which can be partially or completely halogenated and can carry one of the following: cyano, nitro, $C_1$–$C_4$-alkyl, partially or completely halogenated $C_1$–$C_4$-alkyl, $C_2$–$C_4$-alkenyl, partially or completely halogenated $C_2$–$C_4$-alkenyl, $C_1$–$C_4$-alkoxy, phenyl or phenoxy, it being possible for the last two radicals in turn to have one or two of the following substituents: cyano, halogen or $C_1$–$C_4$-alkyl, $C_2$–$C_4$-alkenylene or $C_2$–$C_4$-alkynylene, oxy-($C_1$–$C_4$)-alkylene, thio-($C_1$–$C_4$)-alkylene or $C_1$–$C_4$-alkyleneoxy or carbonyl-($C_1$–$C_4$)-alkylene or $C_1$–$C_4$-alkylenecarbonyl;
- W is $C_1$–$C_4$-alkoxyimino, $C_1$–$C_4$-alkoxymethylene or $C_1$–$C_4$-alkylthiomethylene, excepting compounds where $R^1$ is hydrogen, phenyl or 2,2-dimethyl-3-(2,2-dichlorovinyl) cyclopropyl, $R^2$ to $R^5$ are each hydrogen, Y is carbonyloxymethylene and W is methoxymethylene or methylthiomethylene.

The present invention also relates to processes for preparing these compounds, to their use as fungicides and to their use as insecticides, nematicides and acaricides and to fungicidal agents and agents for controlling pests which contain these compounds as active substances.

EP-A 310 954 discloses, inter alia, fungicidal ortho-substituted phenylacetamides of the type of compounds I, and their phenylacetonitrile precursors, where $R^1$ is hydrogen, phenyl or 2,2-dimethyl-3-(2,2-dichlorovinyl)cyclopropyl, $R^2$ to $R^5$ are each hydrogen, Y is carboxymethylene and W is methoxymethylene or methylthiomethylene. European patent 398 692 discloses similar compounds.

It is an object of the present invention to find novel fungicidal ortho-substituted phenylacetic acid derivatives and novel insecticidal, acaricidal and nematicidal active ingredients.

We have found that this object is achieved by the ortho-substituted phenylacetamides of the formula I defined above.

The specific meanings of the substituents in the novel compounds I are as follows:

$R^1$
- hydrogen;
- branched or unbranched $C_1$–$C_{18}$-alkyl such as methyl, ethyl, n-propyl, isopropyl, 1,1-dimethylpropyl, 2,2-dimethylpropyl, n-butyl, sec-butyl, isobutyl, tert-butyl, 3-methylbutyl, n-pentyl, n-hexyl, n-heptyl, 2,6-dimethylheptyl, n-octyl, n-nonyl, n-decyl, n-pentadecyl, n-heptadecyl and n-octadecyl, preferably $C_1$–$C_{10}$-alkyl;
- $C_3$–$C_8$-cycloalkyl such as cyclopropyl, cyclobutyl, cyclopentyl, cyclohexyl, cycloheptyl and cyclooctyl, each of which can have from one to three substituents selected from a group of 3 halogen atoms such as fluorine, chlorine, bromine and iodine, especially fluorine and chlorine, 3 $C_1$–$C_4$-alkyl groups such as methyl, ethyl, n-propyl, isopropyl, n-butyl, sec-butyl, and tert-butyl, partially or completely halogenated $C_1$–$C_4$-alkenyl such as 2,2-dichloroethenyl, and phenyl which can carry one or two halogen atoms as mentioned above, especially fluorine and chlorine, and/or one $C_1$–$C_4$-alkyl group such as methyl, ethyl, n-propyl, isopropyl, n-butyl and tert-butyl and/or one $C_1$–$C_4$-alkoxy group such as methoxy, ethoxy, n-propoxy, isopropoxy, n-butoxy and tert-butoxy; cyclopropyl, 1-methylcyclopropyl, 2,2-dichlorocyclopropyl, 1-(2,2-dichlorovinyl)cyclopropyl, 1-phenylcyclopropyl, 1-(p-fluorophenyl)-cyclopropyl, cyclohexyl and 1-methylcyclohexyl are preferred;
- $C_2$–$C_{10}$-alkenyl such as vinyl, allyl, 1-propenyl, 2-propenyl, 2-methylpropenyl, 2-butenyl, 1-methylpropenyl, 3-methyl-2-butenyl, 1,3-pentadienyl, 2,6-di-methyl-5-heptenyl and 2,6-dimethyl-1,5-heptadienyl;

C$_2$-C$_4$-alkynyl such as ethynyl and 2-propynyl, which can carry a phenyl radical, eg. 2-phenylethynyl;

C$_1$-C$_4$-alkoxy-C$_1$-C$_4$-alkyl such as methoxymethyl, ethoxymethyl, n-propoxymethyl, isopropoxymethyl, n-butoxymethyl, tert-butoxymethyl, 1-methoxyethyl, 2-methoxyethyl, 1-ethoxyethyl, 2-ethoxyethyl and 2-n-propoxyethyl;

C$_1$-C$_4$-alkoxycarbonyl such as methoxycarbonyl, ethoxycarbonyl, n-propoxycarbonyl, isopropoxycarbonyl, n-butoxycarbonyl and tert-butoxycarbonyl, preferably methoxycarbonyl;

phenyl, phenyl-C$_1$-C$_4$-alkyl such as benzyl, phenethyl, 3-phenyl-n-propyl and 4-phenyl-n-butyl, phenyl-C$_2$-C$_4$-alkenyl such styryl and 2-phenyl-2-propenyl or phenoxy-C$_1$-C$_4$-alkyl such as phenoxymethyl, 2-phenoxyethyl, 3-phenoxypropyl and 4-phenoxybutyl, it being possible for each of the said groups to carry on the phenyl ring a total of from one to five radicals, in particular:

one or two nitro groups,
one or two cyano groups,
up to 5 halogen atoms as mentioned above, especially fluorine and chlorine,
up to 3 C$_1$-C$_4$-alkyl groups as mentioned above,
up to 3 partially or completely halogenated C$_1$-C$_4$-alkyl groups such as fluoromethyl, chloromethyl, trifluoromethyl, trichloromethyl, dichlorofluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl and pentafluoroethyl, especially trifluoromethyl,
up to 3 C$_2$-C$_4$-alkenyl groups such as ethenyl, 1-propenyl, 2-propenyl, 1-methylethenyl, 1-butenyl, 2-butenyl, 3-butenyl, 1-methyl-l-propenyl, 2-methyl1-propenyl, 1-methyl-2-propenyl and 2-methyl-2-propenyl, especially ethenyl and 2-propenyl,
up to 3 partially or completely halogenated C$_2$-C$_4$-alkenyl groups such as 2-fluoroethenyl, 2-chloroethenyl, trifluoroethenyl, trichloroethenyl and 2-chloro-2-propenyl and
up to 3 C$_1$-C$_4$-alkoxygroups such as methoxy, ethoxy, n-propoxy, isopropoxy, n-butoxy and tert-butoxy, phenyl, benzyl, phenoxy, benzyloxy or phenylthio, each of which in turn can have one or two of the following substituents: cyano, halogen as mentioned above, especially fluorine and chlorine, or C$_1$-C$_4$-alkyl as mentioned above;

phenyl, 2-nitrophenyl, 4-nitrophenyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 2-iodophenyl, 2,3-dichlorophenyl, 2,4-dichlorophenyl, 2,5-dichlorophenyl, 2,6-dichlorophenyl, 2,3,4-trichlorophenyl, 2,3,5-trichlorophenyl, 2,3,6-trichlorophenyl, 3,4,5-trichlorophenyl, pentafluorophenyl, pentachlorophenyl, 2-methylphenyl, 3-methylphenyl, 4-methylphenyl, 2-ethylphenyl, 3-ethylphenyl, 4-ethylphenyl, 3-isopropylphenyl, 4-isopropylphenyl, 3-tert-butylphenyl, 4-tert-butylphenyl, 2,3-dimethylphenyl, 2,4-dimethylphenyl, 2,5-dimethylphenyl, 3,4-dimethylphenyl, 3,5-dimethylphenyl, 4-tert-butyl-2-methylphenyl, 3,5-diethylphenyl, 2,3,5-trimethylphenyl, 2,4,6-trimethylphenyl, 4-cyclohexylphenyl, 3-phenoxyphenyl, 4-phenoxyphenyl, 4-phenylthiophenyl, 3-benzyloxyphenyl, 4-benzyloxyphenyl, 2-trifluoromethylphenyl, 3-trifluoromethylphenyl, 4-trifluoromethylphenyl, 2-chloromethylphenyl, 3-chloromethylphenyl, 4-chloromethylphenyl, benzyl, 4-chlorobenzyl, phenethyl, 4-chlorophenethyl, styryl, 4-chlorostyryl, phenoxy, 2-chlorophenoxy, 3-chlorophenoxy, 4-chlorophenoxy, 2-methylphenoxy, 3-methylphenoxy, 4-methylphenoxy, 2-trifluoromethylphenoxy, 3-trifluoromethylphenoxy, 4-trifluoromethylphenoxy, phenoxymethyl and 2-phenoxyethyl are preferred;

a 5- or 6-membered heterocycle with from one to three hetero atoms selected from a group of two oxygen, two sulfur and three nitrogen atoms, excepting compounds with two adjacent oxygen and/or sulfur atoms, it being possible for a benzene ring or a 5- or 6-membered heteroaromatic ring with a nitrogen, oxygen or sulfur atom to be fused on to the heterocycle, for example 2-pyrrolyl, 3-pyrrolyl, 2-furyl, 3-furyl, 2-thienyl, 3-thienyl, 3-pyrazolyl, 4-pyrazolyl, 5-pyrazolyl, 2-oxazolyl, 4-oxazolyl, 5-oxazolyl, 2-benzoxazolyl, 2-thiazolyl, 4-thiazolyl, 5-thiazolyl, benzothiazol-2-yl, 3-isoxazolyl, 4-isoxazolyl, 5-isoxazolyl, 3-isothiazolyl, 4-isothiazolyl, 5-isothiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,3,4-oxadiazol-2-yl, 1,3,4-thiadiazol-2-yl, 1,2,4-triazol-3-yl, 1,3,4-triazol-2-yl, 2-pyridyl, 3-pyridyl, 4-pyridyl, 3-pyridazinyl, 4-pyridazinyl, 2-pyrimidyl, 4-pyrimidyl, 5-pyrimidyl, 2-pyrazinyl, 1,3,5-triazin-2-yl and 1,2,4-triazin-3-yl, it being possible for the heterocycles to carry a halogen atom as mentioned above, especially fluorine and chlorine, one or two C$_1$-C$_4$-alkyl groups as mentioned above, especially methyl, or a phenyl radical, for example 5-chlorobenzothiazol-2-yl, 6-chloro-2-pyridyl, 6-methyl-2-pyridyl, 6-ethyl-2-pyridyl, 6-n-propyl-2-pyridyl, 6-isopropyl-2-pyridyl, 6-n-butyl-2-pyridyl, 6-sec-butyl-2-pyridyl and 6-tert-butyl-2-pyridyl, 6-phenyl-2-pyridyl and 4,8-dimethyl-2-quinolyl; halophenyl, C$_1$-C$_4$-alkylphenyl, di-(C$_1$-C$_4$) -alkylphenyl and benzothiazol-2-yl are particularly preferred; R$^2$, R$^3$ hydrogen, cyano, halogen as mentioned above, especially fluorine and chlorine,
branched or unbranched C$_1$-C$_4$-alkyl as mentioned above, especially methyl, ethyl and isopropyl;
C$_1$-C$_4$-alkoxy as mentioned above, especially methoxy; hydrogen is particularly preferred; R$^4$, R$^5$
hydrogen,
branched or unbranched C$_1$-C$_4$-alkyl as mentioned above, especially methyl, ethyl, n-propyl and n-butyl;
one of the two substituents is C$_1$-C$_4$-alkoxy as mentioned above, especially methoxy;

Y oxygen or sulfur;
—SO—, —SO$_2$—, —CH$_2$—O—SO$_2$—, —N=N—, —O—CO—, —CO—O— or —CO—O—CH$_2$—, preferably —O—CO—, —CO—O— and —CO—O—CH$_2$—;

C$_1$-C$_4$-alkylene which can be partially or completely halogenated, especially fluorinated or chlorinated, and which can also carry one of the following: cyano, nitro, C$_1$-C$_4$-alkyl as mentioned above, partially or completely halogenated C$_1$-C$_4$-alkyl as mentioned above, C$_2$-C$_4$-alkenyl as mentioned above, partially or completely halogenated C$_2$-C$_4$- alkenyl as mentioned above, $C_1$-$C_4$-alkoxy as mentioned above, phenyl or phenoxy, it being possible for the latter two radicals in turn to have one or two of the following substituents: cyano, halogen as mentioned above, especially fluorine and chlorine, or $C_1$-$C_4$-alkyl as mentioned above, especially methyl; methylene or ethylene is preferred;

$C_2$-$C_4$-alkenylene such as ethenylene, 2-propenylene and 2-butenylene, preferably ethenylene;

$C_2$-$C_4$-akynylene such as ethynylene, 2-propynylene and 2-butynylene, preferably ethynylene;

oxy-($C_1$-$C_4$)-alkylene such as oxymethylene, oxyethylene, oxy-n-propylene and oxy-n-butylene, preferably oxymethylene;

thio-($C_1$-$C_4$)-alkylene such as thiomethylene, thioethylene, thio-n-propylene and thio-n-butylene, preferably thiomethylene;

$C_1$-$C_4$-alkyleneoxy such as methyleneoxy, ethyleneoxy, n-propyleneoxyand n-butyleneoxy, preferably methyleneoxy;

carbonyl-($C_1$-$C_4$)-alkylene such as carbonylmethylene, carbonylethylene, carbonyl-n-propylene and carbonyl-n-butylene, preferably carbonylmethylene;

$C_1$-$C_4$-alkylenecarbonyl such as methylenecarbonyl, ethylenecarbonyl, n-propylenecarbonyl and n-butylenecarbonyl, preferably methylenecarbonyl;

carbonyloxy-($C_1$-$C_4$)-alkylene such as carbonyloxymethylene, carbonyloxyethylene, carbonyloxy-n-propylene and carbonyloxy-n-butylene, preferably carbonyloxymethylene;

W $C_1$-$C_4$-alkoxyimino such as methoxyimino, ethoxyimino, n-propoxyimino, isopropoxyimino, n-butoxyimino, secbutoxyimino and tert-butoxyimino, preferably methoxyimino;

$C_1$-$C_4$-alkoxymethylene such as methoxymethylene, ethoxymethylene, n-propoxymethylene, isopropoxymethylene, n-butoxymethylene, sec-butoxymethylene and tert-butoxymethylene, preferably methoxymethylene;

$C_1$-$C_4$-alkylthiomethylene such as methylthiomethylene, ethylthiomethylene, n-propylthiomethylene, isopropylthiomethylene, n-butylthiomethylene, sec-butylthiomethylene and tert-butylthiomethylene, preferably methylthiomethylene; $C_1$-$C_4$-alkoxyimino is preferred.

Particularly suitable ortho-substituted phenylacetamides are shown in Table 1, with compounds with $R^2$ and $R^3$ each being hydrogen, $R^4$ being methyl, $R^5$ being hydrogen and W being methoxyimino or methoxymethylene being particularly preferred. Very particularly suitable are 2-methoxyimino-2-[2-(o-methylphenoxymethyl)phenyl]-acetic acid N-methylamide and 2-methoxyimino-2-[2-(o-methylphenoxymethyl)-phenyl] acetic acid N-methoxyamide.

Preparation of compounds I may result in E/Z isomer mixtures where the two isomers differ by the alkoxy or alkylthio of the substituent W being cis or trans to the amide moiety. If required, the isomers can be separated by conventional methods, eg. by crystallization or chromatography. Compounds with the E configuration (alkoxy or alkylthio of the substituent W trans to the amide moiety) are particularly preferred.

The ortho-substituted phenylacetamides I can be obtained in a variety of ways, preferably by one of the following methods:

a) reaction of phenylacetic acid derivatives II with amines III

L is halogen, especially chlorine and bromine, or $C_1$-$C_4$-alkoxy, especially methoxy.

Preparation of ortho-substituted phenylacetamides I where $R^4$ or $R^5$ is $C_1$-$C_4$-alkoxy preferably starts from a phenylacetyl chloride II (L=Cl).

The reaction is normally carried out by conventional methods (eg. Organikum, 16th edition 1985, pages 409–412) in an inert solvent or diluent, advantageously in the presence of a base.

Particularly suitable solvents or diluents are chlorohydrocarbons such as dichloromethane, ethers such as dioxane, and alcohols such as methanol and ethanol.

Examples of suitable bases are alkali metal hydroxides such as sodium and potassiumhydroxide, alkali metal carbonates such as sodium and potassium carbonate, alkali metal alcoholates such as sodium methylate and sodium ethylate, especially tertiary amines such as triethylamine and heteroaromatic amines such as pyridine and 4-dimethylaminopyridine. However, it is also possible to use the amine III itself as base, for complete reaction in not less than the stoichiometric amount based on II.

All the starting compounds are expediently employed in approximately the stoichiometric ratio, but employed in some cases an excess of one component, of up to about 10 mol %, may be advisable.

If the amine III is used as base, it is present in a larger excess.

The reaction is generally carried out at from 0° to 120° C., in particular at the boiling point of the solvent.

If L is halogen, the reaction can also be carried out in a 2-phase system with phase-transfer catalysis. It is possible and advantageous to use for this mixture of a chlorohydrocarbon such as methylene chloride, aqueous alkali, eg. sodium hydroxide solution, and a phasetransfer catalyst such as tetra-n-butylammonium hydroxide. In this case, the reaction is carried out at, for example, from 10° C. to the boiling point of one of the components of the solvent mixture.

The reaction is normally carried out under atmospheric pressure. An increase or reduction in the pressure is possible but generally has no advantages.

Phenylacetic acid derivatives II where L is halogen are known or can be prepared by known processes (eg. Organikum, 16th edition 1985, pages 415, 622 and 423).

The phenylacetic acid derivatives II where L is C₁-C₄-alkoxy are disclosed in EP-A 178 826 and EP-A 226 917 (X==CH—O-alkyl), EP-A 244 077 (X==CH—S-alkyl) and EP-A 253 213 and EP-A 254 426 (X==N—O-alkyl) or can be prepared by similar processes.

For example, the phenylacetic acid derivatives II with Y=oxymethylene, thiomethylene or —CO—O—CH₂— are obtained by nucleophilic substitution on benzyl halides VI phoric acid, and preferred bases are alkali metal hydroxides such as sodium and potassium hydroxide.

The reaction is normally carried out at from 0° to 200° C., in particular from 20° C. to the boiling point of the solvent.

The statements made for method (a) apply to the ratios of amounts and the pressure.

Phenylacetonitriles of the formula IV are disclosed, for example, in EP-A 310 954 or can be prepared by the methods described therein.

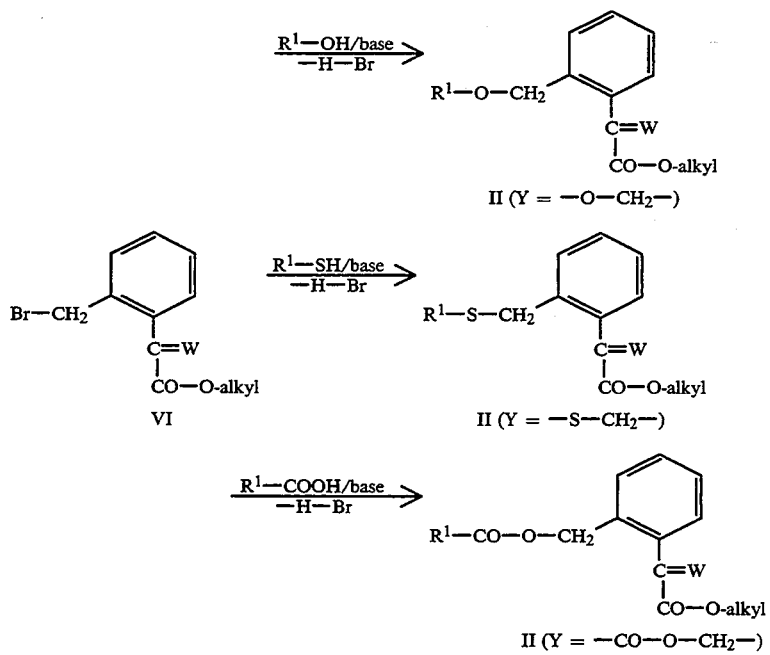

b) Hydrolysis of phenylacetonitriles IV

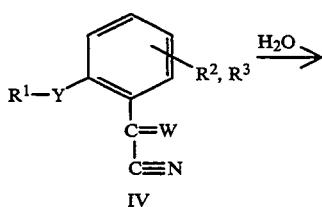

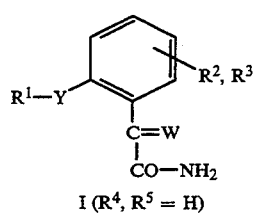

The hydrolysis of the phenylacetonitriles IV is normally catalyzed by acid or base by conventional methods [cf., for example, Beckwith in: Zabicky The Chemistry of Amides, pages 119 to 125 (1970) and Synthesis, 243 (1980)] in an inert solvent or diluent.

Particularly suitable solvents are alcohols such as tert-butanol and ethylene glycol.

Particularly suitable acids are concentrated mineral acids such as hydrochloric acid, sulfuric acid and phos- The ortho-substituted phenylacetamides I where $R^4$ and $R^5$ are each hydrogen can be alkylated on the amide nitrogen by conventional processes [eg. Challis in: Zabicky The Chemistry of Amides, pages 731-857 (1970)]:

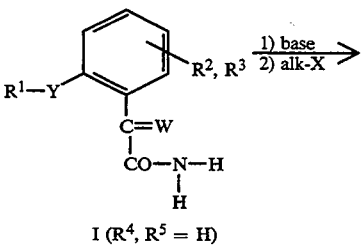

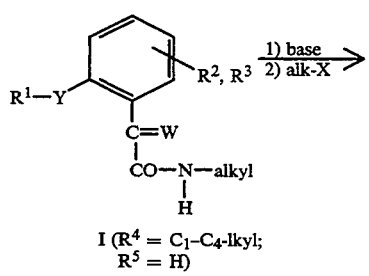

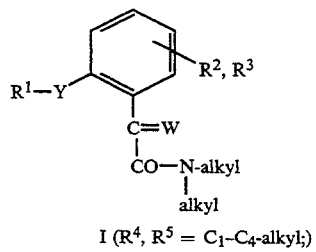

I ($R^4$, $R^5$ = $C_1$-$C_4$-alkyl;)

Alk is $C_1$-$C_4$-alkyl, X is halogen, especially bromine and iodine.

This normally entails conversion of the phenylacetamides I where $R^4$ and $R^5$ are each hydrogen, in an inert solvent or diluent, with a base into the anions and reaction of the latter with an alkyl halide, preferably an alkyl iodide.

Particularly suitable solvents or diluents are ethers such as tetrahydrofuran and dioxane.

Particularly suitable bases are alkali metal hydroxides such as sodium and potassium hydroxide and alkali metal hydrides such as sodium and potassium hydride.

The reaction is generally carried out at from 0° to 100° C., in particular at the boiling point of the solvent.

The statements made for method (a) apply to the ratio of amounts and the pressure.

The ortho-substituted phenylacetamides I are suitable as fungicides and for controlling pests such as insects, nematodes and acarids.

The ortho-substituted phenylacetamides I have excellent activity against a wide spectrum of fungi which are pathogenic for plants, especially from the classes of Ascomycetes and Basidiomycetes. Some of them have systemic activity and can be employed as leaf and soil fungicides.

They are particularly important for controlling a large number of fungi on various crops such as wheat, rye, barley, oats, rice, corn, grass, cotton, soybean, coffee, sugarcane, grapevines, fruit and ornamental plants and vegetables such as cucumbers, beans and pumpkins, and on the seeds of these plants.

They are particularly suitable for controlling the following plant diseases:

Erysiphe graminis (powdery mildew) in cereals,
Erysiphe cichoracearum and Sphaerotheca fuliginea on pumpkins,
Podosphaera leucotricha on apples,
Uncinula necator on grapevines,
Puccinia species on cereals,
Rhizoctonia species on cotton and lawns,
Ustilago species on cereals and sugarcane,
Venturia inaequalis (scab) on apples,
Helminthosporium species on cereals,
Septoria nodorum on wheat,
Botrytis cinerea (gray mold) on strawberries, grapevines,
Cercospora arachidicola on peanuts,
Pseudocercosporella herpotrichoides on wheat, barley,
Pyricularia oryzae on rice,
Phytophthora infestans on potatoes and tomatoes,
Fusarium and Verticillium species on various plants,
Plasmopara viticola on grapevines,
Alternaria species on vegetables and fruit.

The compounds are applied by treating the fungi or the plants, seeds, materials or soil to be protected from fungal attack with a fungicidal amount of the active ingredients. The application is carried out before or after infection of the materials, plants or seeds by the fungi.

The ortho-substituted phenylacetamides I are also suitable for controlling pests from the classes of insects, arachnids and nematodes. They can be employed as pesticides in crop protection and in the hygiene, store protection and veterinary sectors.

The insect pests includes from the order of Lepidoptera, for example Agrotis ypsilon, Agrotis segetum, Alabama argillacea, Anticarsia gemmatalis, Argyresthia conJugella, Autographa gamma, Bupalus piniarius, Cacoecia murinana, Capua reticulana, Cheimatobia brumata, Choristoneura fumiferana, Choristoneura occidentalis, Cirphis unipuncta, Cydia pomonella, Dendrolimus pini, Diaphania nitidalis, Diatraea grandiosella, Earias insulana, Elasmopalpus lignosellus, Eupoecilia ambiguella, Evetria bouliana, Feltia subterranea, Galleria mellonella, Grapholita funebrana, Grapholita molesta, Heliothis armigera, Hellothis virescens, Heliothis zea, Hellula undalis, Hibernia defoliaria, Hyphantria cunea, Hyponomeuta malinellus, Keifferia lycopersicella, Lambdina fiscellaria, Laphygma exigua, Leucoptera coffeella, Leucoptera scitella, Lithocolletis blancardella, Lobesia botrana, Loxostege sticticalis, Lymantria dispar, Lymantria monacha, Lyonetia clerkella, Malacosoma neustria, Mamestra brassicae, Orgyia pseudotsugata, Ostrinia nubilalis, Panolis flamea, Pectinophora gossypiella, Peridroma saucia, Phalera bucephala, Phthorimaea operculella, Phyllocnistis citrella, Pieris brassicae, Plathypena scarbra, Plutella xylostella, Pseudoplusia includens, Phyacionia frustrana, Scrobipalpula absoluta, Sitotroga cerelella, Sparganothis pilleriana, Spodoptera frugiperda, Spodoptera littoralis, Spodoptera litura, Thaumatopoea pityocampa, Tortrix viridana, Trichoplusia ni and Zeiraphera canadensis;

from the order of Coleoptera, for example Agrilus sinuatus, Agriotes lineatus, Agriotes obscurus, Amphimallus solstitialis, Anisandrus dispar, Anthonomus grandis, Anthonomus pomorum, Atomaria linearis, Blastophagus piniperda, Blitophaga undata, Bruchus rufimanus, Bruchus pisorum, Bruchus lentis, Byctiscus betulae, Cassida nebulosa, Cerotoma trifurcata, Ceuthorrhynchus assimilis, Ceuthorrynchus napi, Chaetocnema tibialis, Conoderus vespertinus, Crioceris asparagi, Diabrotica longicornis, Diabrotica 12-punctata, Diabrotica virgifera, Epilachna varivestis, Epitrix hirtipennis, Eutinobothrus brasiliensis, Hylobius abietis, Hypera brunneipennis, Harpera postica, Ips typographus, Lema bilineata, Lema melanopus, Leptinotarsa decemlineata, Limonius californicus, Lissorhoptrus oryzophilus, Melanotus communis, Meligethes aeneus, Melolontha hippocastani, Melolontha melolontha, Onlema oryzae, Otiorrhynchus sulcatus, Otiorrhynchus ovatus, Phaedon cochleariae, Phyllotreta chrysocephala, Phyllophaga sp., Phyllopertha horticola, Phyllotreta nemorum, Phyllotreta striolata, Popillia japonica, Sitona lineatus and Sitophilus granaria;

from the order of Diptera, for example Aedes aegypti, Aedes vexans, Anastrepha ludens, Anopheles maculipennis, Ceratitis capitata, Chrysomya bezziana, Chrysomya hominivorax, Chrysomya macellaria, Contarinia sorghicola, Cordylobia anthropophaga, Culex piplens, Dacus cucurbitae, Dacus oleae, Dasineura brassicae, Fannia canicularis, Gasterophilus intestinalis, Glossia morsitans, Haematobia irritans, Haplodiplosis equestris, Hylemyia platura, Hypoderma lineata, Liriomyza sativae, Liriomyza trifolii, Lucilia caprina, Lucilia cuprina, Lucilia sericata, Lycoria pectoralis, Mayetiola destructor, Musca domestica, Muscina stabulans, Oestrus ovis, Oscinella frit, Pegomya hysocyami, Phorbia antiqua, Phorbia brassicae, Phorbia coarctata, Rhagoletis cerasi, Rhagoletis pomonella, Tabanus bovinus, Tipula oleracea and Tipula paludosa;

from the order of Thysanoptera, for example Frankliniella fusca, Franklinleila occidentalis, Franklinleila tritici, Scirtothrips citri, Thrips oryzae, Thrips palmi and Thrips tabaci;

from the order of Hymenoptera, for example Athalia rosae, Atta cephalotes, Atta sexdens, Atta texana, Hoplocampa minuta, Hoplocampa testudinea, Monomorium pharaonis, Solenopsis geminata and Solenopsis invicta;

from the order of Heteroptera, for example Acrosternum hilare, Blissus leucopterus, Cyrtopeltis notatus, Dysdercus cinqulatus, Dysdercus intermedius, Eurygaster integriceps, Euchistus impictiventris, Leptoglossus phyllopus, Lygus lineolaris, Lyqus pratensis, Nezara viridula, Piesma quadrata, Solubea insularis and Thyanta perditor;

from the order of Homoptera, for example Acyrthosiphon onobrychis, Adelges laricis, Aphidula nasturtii, Aphis fabae, Aphis pomi, Aphis sambuci, Brachycaudus cardui, Brevicoryne brassicae, Cerosipha gossypii, Dreyfusia nordmannianae, Dreyfusia piceae, Dyasphis radicola, Dysaulacorthum pseudosolani, Empoasca fabae, Macrosiphum avenae, Macrosiphum euphorbiae, Macrosiphon rosae, Megoura viciae, Metopolophiumdirhodum, Myzodes persicae, Myzus cerasi, Nilaparvata lugens, Pemphiqus bursarius, Perkinsleila saccharicida, Phorodon humuli, Psylla mali, Psylla piri, Rhopalomyzus ascalonicus, Rhopalosiphum maidis, Sappaphis mala, Sappaphis mali, Schizaphis graminum, Schizoneura lanuginosa, Trialeurodes vaporariorum and Viteus vitifolii;

from the order of Isoptera, for example Calotermes flavicollis, Leucotermes flavipes, Reticulitermes lucifugus and Termes natalensis;

from the order of Orthoptera, for example Acheta domestica, Blatta orientalis, Blattella germanica, Forficula auricularia, Gryllotalpa gryllotalpa, Locusta migratoria, Melanoplus birittatus, Melanoplus femurrubrum, Melanoplus mexicanus, Melanoplus sanguinipes, Melanoplus spretus, Nomadacris septemfasciata, Periplaneta americana, Schistocerca americana, Schistocerca peregrina, Stauronotus maroccanus and Tachycines asynamorus;

from the class of Arachnoidea, for example arachnids (Acarina) such as Amblyomma americanum, Amblyomma variegatum, Argas persicus, Boophilus annulatus, Boophilus decoloratus, Boophilus microplus, Brevipalpus phoenicis, Bryobia praetiosa, Dermacentor silvarum, Eotetranychus carpini, Eriophyes sheldoni, Hyalomma truncatum, Ixodes ricinus, Ixodes rubicundus, Ornithodorus moubata, Otobins megnini, Paratetranychus pilosus, Permanyssus gallinae, Phyllocaptrata oleivora, Polyphagotarsonemus latus, Psoroptes ovis, Rhipicephalus appendiculatus, Rhipicephalus evertsi, Sarcoptes scabiei, Tetranychus cinnabarinus, Tetranychus kanzawai, Tetranychus pacificus, Tetranychus telarius and Tetranychus urticae;

from the class of nematodes, for example root knot nematodes, eg. Meloidogyne hapla, Meloidogyne incognita, Meloidogyne Javanica, cyst-forming nematodes, eg. Globodera rostochiensis, Heterodera avenae, Heterodera glycinae, Heterodera schatii, Heterodera triflolii, stem and leaf eelworms, eg. Belonolaimus longicaudatus, Ditylenchus destructor, Ditylenchus dipsaci, Heliocotylenchus multicinctus, Longidorus elongatus, Radopholus similis, Rotylenchus robustus, Trichodorus primitivus, Tylenchorhynchus claytoni, Tylenchorhynchus dubius, Pratylenchus neglectus, Pratylenchus penetrans, Pratylenchus curvitatus and Pratylenchus goodeyi.

The active ingredients can be converted into conventional formulations such as solutions, emulsions, suspensions, dusts, powders, pastes and granules. The application forms depend on the purposes for which they are used; they ought in every case to ensure fine and uniform distribution of the ortho-substituted phenylacetamide. The formulations are prepared in a conventional manner, eg. by extending the active ingredient with solvents and/or carriers, if required using emulsifiers and dispersants, it being possible to use other organic solvents as auxiliary solvents when water is used as diluent.

Suitable for preparing directly sprayable solutions, emulsions, pastes or oil dispersions are mineral oil fractions of medium to high boiling point such as kerosine or diesel oil, also coaltar oils and oils of vegetable or animal origin, aliphatic, cyclic and aromatic hydrocarbons, eg. benzene, toluene, xylene, paraffin, tetrahydronaphthalene, alkylated naphthalenes or derivatives thereof, methanol, ethanol, propanol, butanol, chloroform, tetrachloromethane, cyclohexanol, cyclohexanone, chlorobenzene, isophorone, highly polar solvents, eg. dimethylformamide, dimethyl sulfoxide, N-methylpyrrolidone and water.

Aqueous application forms can be prepared from emulsion concentrates, pastes or wettable powders (oil dispersions) by adding water. To prepare emulsions, pastes or oil dispersions, the substances can be homogenized, as such or dissolved in an oil or solvent, using wetting agents, adhesion promoters, dispersants or emulsifiers in water. However, concentrates suitable for dilution with water can also be prepared from active substance, wetting agent, adhesion promoter, dispersant or emulsifier and, possibly, solvent or oil.

Suitable surfactants are alkali metal, alkaline earth metal and ammonium salts of ligninsulfonic acid, naphthalenesulfonic acid, phenolsulfonic acid, dibutylnaphthalenesulfonic acid, alkylarylsulfonates, alkyl sulfates, alkylsulfonates, fatty alcohol sulfates and fatty acids and their alkali metal and alkaline earth metal salts, salts of sulfated fatty alcohol glycol ethers, products of the condensation of sulfonated naphthalene and naphthalene derivatives with formaldehyde, products of the condensation of naphthalene or naphthalenesulfonic acid with phenol and formaldehyde, polyoxyethylene octylphenol ether, ethoxylated isooctylphenol, octylphenol, nonylphenol, alkylphenol polyglycol ether, tributylphenyl polyglycol ether, alkylaryl polyether alcohols, isotridecyl alcohol, fatty alcohol/ethylene oxide condensates, ethoxylated castor oil, polyoxyethylene alkyl ether, ethoxylated polyoxypropylene, lauryl alcohol polyglycol ether acetal, sorbitol ester, lignin sulfite waste liquors and methylcellulose.

Powders and dusting and broadcasting agents can be prepared by mixing or grinding together the active substances with a solid carrier.

The concentrations of active ingredient in the formulations ready for use can vary within wide limits.

The agents very generally contain from 0.0001 to 95, preferably from 0.01 to 90, % by weight of active ingredient.

Formulations containing more than 95% by weight of active ingredient can be applied very successfully by the ultra low volume (ULV) method, in which case even the active ingredient without additives can be used.

Examples of such formulations are:

I. a solution of 90 parts by weight of compound No. 87 and 10 parts by weight of N-methyl-α-pyrrolidone, which is suitable for application in the form of very small drops;

II. a mixture of 20 parts by weight of compound No. 93, 80 parts by weight of xylene, 10 parts by weight of the adduct of 8 to 10 moles of ethylene oxide and 1 mole of oleic acid N-monoethanolamide, 5 parts by weight of calcium dodecylbenzenesulfonate, 5 parts by weight of the adduct of 40 moles of ethylene oxide and 1 mole of castor oil; a fine dispersion of the solution in water is used;

III. An aqueous dispersion of 20 parts by weight of compound No. 133, 40 parts by weight of cyclohexanone, 30 parts by weight of isobutanol, 20 parts by weight of the adduct of 40 moles of ethylene oxide and 1 mole of castor oil;

IV. an aqueous dispersion of 20 parts by weight of compound No. 242, 25 parts by weight of cyclohexanol, 65 parts by weight of a mineral oil fraction of boiling point 210° to 280° C. and 10 parts by weight of the adduct of 40 moles of ethylene oxide and 1 mole of castor oil;

V. a mixture, ground in a hammer mill, of 80 parts by weight of compound No. 252, 3 parts by weight of sodium diisobutylnaphthalene-α-sulfonate, 10 parts by weight of the sodium salt of a ligninsulfonic acid from a sulfite waste liquor and 7 parts by weight of powdered silica gel; a fine dispersion of the mixture in water can be sprayed;

VI. an intimate mixture of 3 parts by weight of compound No. 449 and 97 parts by weight of finely divided kaolin; this dusting agent contains 3% by weight of active ingredient;

VII. an intimate mixture of 30 parts by weight of compound No. 494, 92 parts by weight of powdered silica gel and 8 parts by weight of liquid paraffin which has been sprayed on to the surface of this silica gel; this formulation makes the active ingredient adhere well;

VIII. a stable aqueous dispersion of 40 parts by weight of compound No. 585, 10 parts by weight of the sodium salt of a phenolsulfonic acid/urea/-formaldehyde condensate, 2 parts by weight of silica gel and 48 parts by weight of water, which can be further diluted;

IX. a stable oily dispersion of 20 parts by weight of compound No. 587, 2 parts by weight of calcium dodecylbenzenesulfonate, 8 parts by weight of fatty alcohol polyglycol ether, 20 parts by weight of the sodium salt of a phenolsulfonic acid/urea/-formaldehyde condensate and 68 parts by weight of a liquid paraffin.

Granules, eg. coated, impregnated or homogeneous granules, can be prepared by binding the active ingredients to solid carriers. Examples of solid carriers are mineral earths such as silica gel, silicic acids, silicates, talc, kaolin, attapulgite, limestone, lime, chalk, bole, loess, clay, dolomite, diatomaceous earth, calcium and magnesium sulfate, magnesium oxide, ground plastics, fertilizers such as, for example, ammonium sulfate, ammoniumphosphate, ammoniumnitrate, ureas and vegetable products such as cereal flour, bark meal, wood meal and nutshell meal, cellulose powders and other solid carriers.

The application rates in fungicidal agents depend on the nature of the desired effect and range from 0.02 to 3 kg of active ingredient per ha. The novel compounds can also be used to protect materials (wood), eg. against Paecilomyces variotii.

For treating seeds, in general from 0.001 to 50 g, preferably 0.01 to 10 g, of active ingredient are required per kilogram of seeds.

The application rate for controlling insects in the open is from 0.02 to 10, preferably 0.1 to 2.0 kg/ha active ingredient.

In these application forms, the novel agents can also be mixed with other active ingredients, eg. with herbicides, insecticides, growth regulators, fungicides or fertilizers. These agents can be added to the novel agents in the ratio of from 1:10 to 10:1 by weight, where appropriate just before application (tank mix). Mixing with fungicides or insecticides in many cases results in an extension of the spectrum of action.

The agents and the formulations prepared therefrom ready for use, such as solutions, emulsions, suspensions, powders, dusts, pastes or granules, are applied in a conventional manner, for example by spraying, atomizing, dusting, broadcasting, treating seeds or watering.

PREPARATION EXAMPLES

Example 1

2-Methoxyimino-2-[2-(m-chlorophenoxymethyl)-phenyl]acetamide

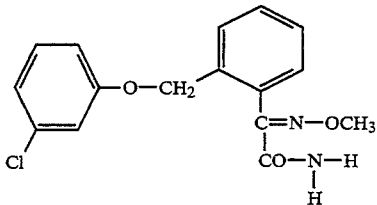

(compound No. 89)

7.0 g (23 mmol) of 2-methoxyimino-2-[2-(m-chlorophenoxymethyl)phenyl]acetonitrile were added to a mixture of 50 ml of glycol and 10 ml of a 25% by weight aqueous solution of potassiumhydroxide, and the reaction mixture was then heated at 80° C. for 2 hours. The solid was then separated off, washed with methyl tert-butyl ether and dried. Yield: 58%; $^1$H-NMR (in CDCl$_3$, TMS as standard): d=4.00(s,3H); 5.18(s,2H); 6.10(sbr, 1H); 6.75(sbr, 1H); 6.78(d, 1H); 6.92(m,2H); 7.10–7.50(m,5H).

Example 2

2-Methoxyimino-2-[2-(o,p-dimethylphenoxymethyl)-phenyl]-acetic acid N-methylamide (compound No. 494)

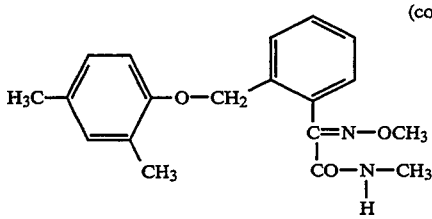

0.465 g (15 mmol) of monomethylamine dried over potassium hydroxide was passed at about 25° C. into a solution of 5.0 g (15 mmol) of 2-methoxyimino-2-[2-(o,pdimethylphenoxymethyl)phenyl]acetyl chloride in 30 ml of dichloromethane. This mixture was stirred for one hour and then diluted with 70 ml of dichloromethane. Byproducts were extracted with 100 ml of water and then the organic phase was worked up in a conventional manner to give the product. Yield: 88% (oil); $^1$H-NMR (in CDCl$_3$, TMS as standard): d=2.20(s,3H); 2.25(s,3H); 2.90(d,3H); 3.94(s,3H); 4.93(s,2H); 6.70–7.60(m,7H).

Example 3

2-Methoxyimino-2-(2-benzyloxyphenyl)acetic acid N,N-dimethylamide (compound No. 206)

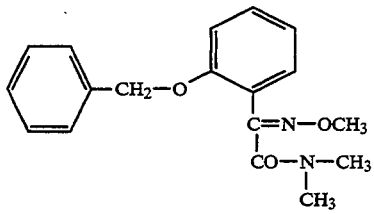

A solution of 4.9 g (16.4 mmol) of methyl 2-methoxyimino-2-(2-benzyloxyphenyl)acetate and 0.9 g (20 mmol) of dimethylamine in 20 ml of methanol was stirred at about 25° C. for 60 hours. After removal of the solvent, the crude product was purified by chromatography on silica gel (methyl tert-butyl ether/n-hexane mixture as eluent). Yield: 66%; $^1$H-NMR (in CDCl$_3$, TMS as standard): d=3.38(s,3H); 3.49(s,3H); 4.01(s,3H); 5.03(s,2H); 6.90–7.10(m,2H); 7.30–7.40(m,6H); 8.75(d, 1H).

Example 4

2-Methoxyimino-2-[2-(o,p-dimethylphenoxymethyl)-phenyl]acetic acid N,N-dimethylamide (compound No. 252)

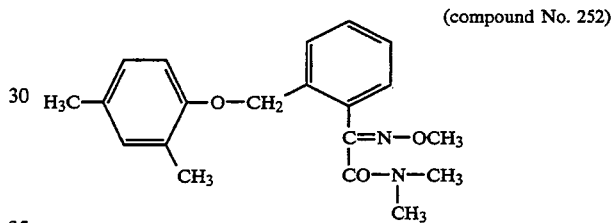

0.675 g (15 mmol) of dried dimethylamine was reacted with 5.0 g (15 mmol) of 2-methoxyimino-2-[2-(o,pdimethylphenoxymethyl)phenyl]acetyl chloride in a similar manner to Example 2. Yield: 78% (oil); $^1$H-NMR (in CDCl$_3$, TMS as standard ): d=2.20(s,3H); 2.23(s,3H); 3.02(s,3H); 3.18(s,3H); 3.95(s,3H); 5.02(s,2H); 6.60–7.60(m,7H).

Further final products I which were or can be prepared in the same way are listed in Table 1.

TABLE (R², R³ = H)

| No. | Y | R¹ | R⁴ | R⁵ | W | Physical data |
|---|---|---|---|---|---|---|
| 1 | CH₂ | H | H | H | N—OCH₃ | |
| 2 | CHCl | H | H | H | N—OCH₃ | |
| 3 | CHBr | H | H | H | N—OCH₃ | |
| 4 | CHI | H | H | H | N—OCH₃ | |
| 5 | CH₂—CH₂ | C₆H₅ | H | H | N—OCH₃ | |
| 6 | CH₂—CH₂ | 2-F—C₆H₄ | H | H | N—OCH₃ | |
| 7 | CH₂—CH₂ | 3-F—C₆H₄ | H | H | N—OCH₃ | |
| 8 | CH₂—CH₂ | 4-F—C₆H₄ | H | H | N—OCH₃ | |
| 9 | CH₂—CH₂ | 2-Cl—C₆H₄ | H | H | N—OCH₃ | |
| 10 | CH₂—CH₂ | 3-Cl—C₆H₄ | H | H | N—OCH₃ | |
| 11 | CH₂—CH₂ | 4-Cl—C₆H₄ | H | H | N—OCH₃ | |
| 12 | CH₂—CH₂ | 2-Br—C₆H₄ | H | H | N—OCH₃ | |
| 13 | CH₂—CH₂ | 4-Br—C₆H₄ | H | H | N—OCH₃ | |
| 14 | CH₂—CH₂ | 2-I—C₆H₄ | H | H | N—OCH₃ | |
| 15 | CH₂—CH₂ | 2-CH₃—C₆H₄ | H | H | N—OCH₃ | |
| 16 | CH₂—CH₂ | 3-CH₃—C₆H₄ | H | H | N—OCH₃ | |
| 17 | CH₂—CH₂ | 4-CH₃—C₆H₄ | H | H | N—OCH₃ | |
| 18 | CH₂—CH₂ | 2-OCH₃—C₆H₄ | H | H | N—OCH₃ | |
| 19 | CH₂—CH₂ | 3-OCH₃—C₆H₄ | H | H | N—OCH₃ | |
| 20 | CH₂—CH₂ | 4-OCH₃—C₆H₄ | H | H | N—OCH₃ | |
| 21 | CH₂—CH₂ | 2-CF₃—C₆H₄ | H | H | N—OCH₃ | |
| 22 | CH₂—CH₂ | 3-CF₃—C₆H₄ | H | H | N—OCH₃ | |
| 23 | CH₂—CH₂ | 4-CF₃—C₆H₄ | H | H | N—OCH₃ | |
| 24 | CH₂—CH₂ | 2,4-Cl₂—C₆H₃ | H | H | N—OCH₃ | |
| 25 | CH₂—CH₂ | 2,4-(CH₃)₂—C₆H₃ | H | H | N—OCH₃ | |
| 26 | CH₂—CH₂ | 2,4,6-(CH₃)₃—C₆H₂ | H | H | N—OCH₃ | |
| 27 | CH₂—CH₂ | Pyridin-3-yl | H | H | N—OCH₃ | |
| 28 | CH₂—CH₂ | Furan-2-yl | H | H | N—OCH₃ | |
| 29 | CH₂—CH₂ | 6-CH₃-Pyridin-2-yl | H | H | N—OCH₃ | |
| 30 | CH₂—CH₂ | Benzothiazol-2-yl | H | H | N—OCH₃ | |
| 31 | CH=CH | C₆H₅ | H | H | N—OCH₃ | |
| 32 | CH=CH | 2-F—C₆H₄ | H | H | N—OCH₃ | |
| 33 | CH=CH | 3-F—C₆H₄ | H | H | N—OCH₃ | |
| 34 | CH=CH | 4-F—C₆H₄ | H | H | N—OCH₃ | |
| 35 | CH=CH | 2-Cl—C₆H₄ | H | H | N—OCH₃ | |
| 36 | CH=CH | 3-Cl—C₆H₄ | H | H | N—OCH₃ | |
| 37 | CH=CH | 4-Cl—C₆H₄ | H | H | N—OCH₃ | |
| 38 | CH=CH | 2-Br—C₆H₄ | H | H | N—OCH₃ | |
| 39 | CH=CH | 4-Br—C₆H₄ | H | H | N—OCH₃ | |
| 40 | CH=CH | 2-I—C₆H₄ | H | H | N—OCH₃ | |
| 41 | CH=CH | 2-CH₃—C₆H₄ | H | H | N—OCH₃ | |

TABLE-continued ($R^2$, $R^3$ = H)

| No. | Y | $R^1$ | $R^4$ | $R^5$ | W | Physical data |
|---|---|---|---|---|---|---|
| 42 | CH=CH | 3-$CH_3$—$C_6H_4$ | H | H | N—$OCH_3$ | |
| 43 | CH=CH | 4-$CH_3$—$C_6H_4$ | H | H | N—$OCH_3$ | |
| 44 | CH=CH | 2-$OCH_3$—$C_6H_4$ | H | H | N—$OCH_3$ | |
| 45 | CH=CH | 3-$OCH_3$—$C_6H_4$ | H | H | N—$OCH_3$ | |
| 46 | CH=CH | 4-$OCH_3$—$C_6H_4$ | H | H | N—$OCH_3$ | |
| 47 | CH=CH | 2-$CF_3$—$C_6H_4$ | H | H | N—$OCH_3$ | |
| 48 | CH=CH | 3-$CF_3$—$C_6H_4$ | H | H | N—$OCH_3$ | |
| 49 | CH=CH | 4-$CF_3$—$C_6H_4$ | H | H | N—$OCH_3$ | |
| 50 | CH=CH | 2,4-$Cl_2$—$C_6H_3$ | H | H | N—$OCH_3$ | |
| 51 | CH=CH | 2,4-$(CH_3)_2$—$C_6H_3$ | H | H | N—$OCH_3$ | |
| 52 | CH=CH | 2,4,6-$(CH_3)_3$—$C_6H_2$ | H | H | N—$OCH_3$ | |
| 53 | CH=CH | Pyridin-3-yl | H | H | N—$OCH_3$ | |
| 54 | CH=CH | Furan-2-yl | H | H | N—$OCH_3$ | |
| 55 | CH=CH | 6-$CH_3$-Pyridin-2-yl | H | H | N—$OCH_3$ | |
| 56 | CH=CH | Benzothiazol-2-yl | H | H | N—$OCH_3$ | |
| 57 | $CH_2O$ | $C_6H_5$ | H | H | N—$OCH_3$ | |
| 58 | $CH_2O$ | 2-F—$C_6H_4$ | H | H | N—$OCH_3$ | |
| 59 | $CH_2O$ | 3-F—$C_6H_4$ | H | H | N—$OCH_3$ | |
| 60 | $CH_2O$ | 4-F—$C_6H_4$ | H | H | N—$OCH_3$ | |
| 61 | $CH_2O$ | 2-Cl—$C_6H_4$ | H | H | N—$OCH_3$ | |
| 62 | $CH_2O$ | 3-Cl—$C_6H_4$ | H | H | N—$OCH_3$ | |
| 63 | $CH_2O$ | 4-Cl—$C_6H_4$ | H | H | N—$OCH_3$ | |
| 64 | $CH_2O$ | 2-Br—$C_6H_4$ | H | H | N—$OCH_3$ | |
| 65 | $CH_2O$ | 4-Br—$C_6H_4$ | H | H | N—$OCH_3$ | |
| 66 | $CH_2O$ | 2-I—$C_6H_4$ | H | H | N—$OCH_3$ | |
| 67 | $CH_2O$ | 2-$CH_3$—$C_6H_4$ | H | H | N—$OCH_3$ | |
| 68 | $CH_2O$ | 3-$CH_3$—$C_6H_4$ | H | H | N—$OCH_3$ | |
| 69 | $CH_2O$ | 4-$CH_3$—$C_6H_4$ | H | H | N—$OCH_3$ | |
| 70 | $CH_2O$ | 2-$OCH_3$—$C_6H_4$ | H | H | N—$OCH_3$ | |
| 71 | $CH_2O$ | 3-$OCH_3$—$C_6H_4$ | H | H | N—$OCH_3$ | |
| 72 | $CH_2O$ | 4-$OCH_3$—$C_6H_4$ | H | H | N—$OCH_3$ | |
| 73 | $CH_2O$ | 2-$CF_3$—$C_6H_4$ | H | H | N—$OCH_3$ | |
| 74 | $CH_2O$ | 3-$CF_3$—$C_6H_4$ | H | H | N—$OCH_3$ | |
| 75 | $CH_2O$ | 4-$CF_3$—$C_6H_4$ | H | H | N—$OCH_3$ | |
| 76 | $CH_2O$ | 2,4-$Cl_2$—$C_6H_3$ | H | H | N—$OCH_3$ | |
| 77 | $CH_2O$ | 2,4-$(CH_3)_2$—$C_6H_3$ | H | H | N—$OCH_3$ | |
| 78 | $CH_2O$ | 2,4,6-$(CH_3)_3$—$C_6H_2$ | H | H | N—$OCH_3$ | |
| 79 | $CH_2O$ | Pyridin-3-yl | H | H | N—$OCH_3$ | |
| 80 | $CH_2O$ | Furan-2-yl | H | H | N—$OCH_3$ | |
| 81 | $CH_2O$ | 6-$CH_3$-Pyridin-2-yl | H | H | N—$OCH_3$ | |
| 82 | $CH_2O$ | Benzothiazol-2-yl | H | H | N—$OCH_3$ | |

TABLE-continued

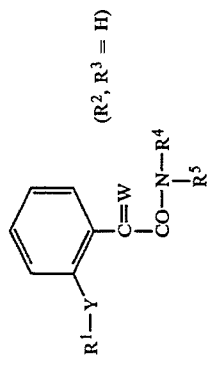

(R² , R³ = H)

| No. | Y | R¹ | R⁴ | R⁵ | W | Physical data |
|---|---|---|---|---|---|---|
| 83 | O—CH₂ | H | H | H | N—OCH₃ | |
| 84 | O—CH₂ | C₆H₅ | H | H | N—OCH₃ | |
| 85 | O—CH₂ | 2-F—C₆H₄ | H | H | N—OCH₃ | |
| 86 | O—CH₂ | 3-F—C₆H₄ | H | H | N—OCH₃ | |
| 87 | O—CH₂ | 4-F—C₆H₄ | H | H | N—OCH₃ | M.p. 127–9° C.; IR(KBr): 3371, 3184, 1652, 1507, 1249, 1050, 824 cm⁻¹ |
| 88 | O—CH₂ | 2-Cl—C₆H₄ | H | H | N—OCH₃ | |
| 89 | O—CH₂ | 3-Cl—C₆H₄ | H | H | N—OCH₃ | M.p. 104–5° C.; IR(KBr): 3416, 1663, 1559, 1482, 1249, 1045, 904, 775 cm⁻¹ |
| 90 | O—CH₂ | 4-Cl—C₆H₄ | H | H | N—OCH₃ | M.p. 105–10° C. |
| 91 | O—CH₂ | 2-Br—C₆H₄ | H | H | N—OCH₃ | M.p. 88–90° C.; 1H-NMR(CDCl₃): δ=4.13(s, 3H), 5.35 (s2H), 6.85(m, 2H), 7.25(m, 1H), 7.58(m, 3H), 7.78 (d, 1H), 7.86(d, 1H) |
| 92 | O—CH₂ | 4-Br—C₆H₄ | H | H | N—OCH₃ | M.p. 148–50° C.; IR(KBr): 3373, 1652, 1474, 1249, 1055, 749 |
| 93 | O—CH₂ | 2-I—C₆H₄ | H | H | N—OCH₃ | M.p. 100–2° C.; IR(KBr): 1674, 1510, 1239, 1042, 814 |
| 94 | O—CH₂ | 2-CH₃—C₆H₄ | H | H | N—OCH₃ | |
| 95 | O—CH₂ | 3-CH₃—C₆H₄ | H | H | N—OCH₃ | |
| 96 | O—CH₂ | 4-CH₃—C₆H₄ | H | H | N—OCH₃ | |
| 97 | O—CH₂ | 2-OCH₃—C₆H₄ | H | H | N—OCH₃ | |
| 98 | O—CH₂ | 3-OCH₃—C₆H₄ | H | H | N—OCH₃ | |
| 99 | O—CH₂ | 4-OCH₃—C₆H₄ | H | H | N—OCH₃ | |
| 100 | O—CH₂ | 2-CF₃—C₆H₄ | H | H | N—OCH₃ | |
| 101 | O—CH₂ | 3-CF₃—C₆H₄ | H | H | N—OCH₃ | |
| 102 | O—CH₂ | 4-CF₃—C₆H₄ | H | H | N—OCH₃ | |
| 103 | O—CH₂ | 2,4-Cl₂—C₆H₃ | H | H | N—OCH₃ | |
| 104 | O—CH₂ | 2,4,6-(CH₃)₃—C₆H₂ | H | H | N—OCH₃ | |
| 105 | O—CH₂ | 2-CH₃,4-Cl—C₆H₃ | H | H | N—OCH₃ | |
| 106 | O—CH₂ | 3-t-C₄H₉—C₆H₄ | H | H | N—OCH₃ | |
| 107 | O—CH₂ | 4-C₆H₅—C₆H₄ | H | H | N—OCH₃ | |
| 108 | O—CH₂ | 2-Cl, 4-CH₃—C₆H₃ | H | H | N—OCH₃ | |
| 109 | O—CH₂ | Pyridin-2-yl | H | H | N—OCH₃ | |
| 110 | O—CH₂ | 6-CH₃-Pyridin-2-yl | H | H | N—OCH₃ | |
| 111 | O—CH₂ | 2-Cl—Pyridin-2-yl | H | H | N—OCH₃ | |
| 112 | O—CH₂ | Benzothiazol-2-yl | H | H | N—OCH₃ | |
| 113 | O | H | H | H | N—OCH₃ | |
| 114 | O | C₆H₅ | H | H | N—OCH₃ | |
| 115 | O | 3-C₆H₅—C₆H₄ | H | H | N—OCH₃ | |
| 116 | O | 3-OC₃H₄—C₆H₄ | H | H | N—OCH₃ | |
| 117 | O | Pyridin-2-yl | H | H | N—OCH₃ | |

TABLE-continued

Structure: $R^1-Y$ substituted phenyl with $C=W$ and $CO-N(R^4)(R^5)$ group ($R^2, R^3 = H$)

| No. | Y | R¹ | R⁴ | R⁵ | W | Physical data |
|-----|---|----|----|----|----|---------------|
| 119 | O | 6-C₆H₅-Pyridin-2-yl | H | H | N—OCH₃ | |
| 120 | O | CH₂—CH=CH₂ | H | H | N—OCH₃ | |
| 121 | O | 3-C₆H₅O—C₆H₄ | H | H | N—OCH₃ | |
| 122 | O | 3-C₆H₅S—C₆H₄ | H | H | N—OCH₃ | |
| 123 | O | 3-C₆H₅CH₂O—C₆H₄ | H | H | N—OCH₃ | |
| 124 | C≡C | CH₃ | H | H | N—OCH₃ | |
| 125 | C≡C | C₆H₅ | H | H | N—OCH₃ | |
| 126 | S | C₆H₅ | H | H | N—OCH₃ | |
| 127 | S | 2-Cl—C₆H₄ | H | H | N—OCH₃ | |
| 128 | S—CH₂ | C₆H₅ | H | H | N—OCH₃ | |
| 129 | S—CH₂ | 4-Cl—C₆H₄ | H | H | N—OCH₃ | |
| 130 | S—CH₂ | 4-CH₃—C₆H₄ | H | H | N—OCH₃ | |
| 131 | S—CH₂ | 6-CH₃-Pyridin-2-yl | H | H | N—OCH₃ | |
| 132 | S—CH₂ | 6-Cl-Pyridin-2-yl | H | H | N—OCH₃ | |
| 133 | S—CH₂ | Benzothiazol-2-yl | H | H | N—OCH₃ | M.p. 171–8° C.; IR(KBr): 3388, 3155, 1672, 1650, 1429, 1037, 989, 748 cm⁻¹ |
| 134 | S—CH₂ | 5-Cl—Benzothiazol-2-yl | H | H | N—OCH₃ | |
| 135 | S—CH₂ | 6-Cl—Benzothiazol-2-yl | H | H | N—OCH₃ | |
| 136 | —CO—O— | CH₃ | H | H | N—OCH₃ | |
| 137 | —CO—O— | C₆H₅ | H | H | N—OCH₃ | |
| 138 | —O—O— | CH₃ | H | H | N—OCH₃ | |
| 139 | —O—O— | C₆H₅ | H | H | N—OCH₃ | |
| 140 | —O—CO— | H | H | H | N—OCH₃ | |
| 141 | —O—CO— | CH₃ | H | H | N—OCH₃ | |
| 142 | —CO—CH₂— | CH₃ | H | H | N—OCH₃ | |
| 143 | —CO—CH₂— | C₆H₅ | H | H | N—OCH₃ | |
| 144 | —CO—CH₂— | 2-CH₃—C₆H₄ | H | H | N—OCH₃ | |
| 145 | —CO—CH₂— | 2,4-(CH₃)₂C₆H₃ | H | H | N—OCH₃ | |
| 146 | —CO—CH₂— | 2-Cl—C₆H₄ | H | H | N—OCH₃ | |
| 147 | —CH₂—CO— | H | H | H | N—OCH₃ | |
| 148 | —CH₂—CO— | C₆H₅ | H | H | N—OCH₃ | |
| 149 | —N=N— | C₆H₅ | H | H | N—OCH₃ | |
| 150 | CH₂ | H | CH₃ | H | N—OCH₃ | |
| 150 | CH₂ | H | CH₃ | H | N—OCH₃ | |
| 151 | CHCl | H | CH₃ | H | N—OCH₃ | |
| 152 | CHBr | H | CH₃ | H | N—OCH₃ | |
| 153 | CHI | H | CH₃ | H | N—OCH₃ | |
| 154 | CH₂—CH₂ | C₆H₅ | CH₃ | CH₃ | N—OCH₃ | |
| 155 | CH₂—CH₂ | 2-F—C₆H₄ | CH₃ | CH₃ | N—OCH₃ | |
| 156 | CH₂—CH₂ | 3-F—C₆H₄ | CH₃ | CH₃ | N—OCH₃ | |
| 157 | CH₂—CH₂ | 4-F—C₆H₄ | CH₃ | CH₃ | N—OCH₃ | |

TABLE-continued

| No. | Y | R¹ | R⁴ | R⁵ | W | Physical data |
|---|---|---|---|---|---|---|
| 158 | CH₂—CH₂ | 2-Cl—C₆H₄ | CH₃ | CH₃ | N—OCH₃ | |
| 159 | CH₂—CH₂ | 3-Cl—C₆H₄ | CH₃ | CH₃ | N—OCH₃ | |
| 160 | CH₂—CH₂ | 4-Cl—C₆H₄ | CH₃ | CH₃ | N—OCH₃ | |
| 161 | CH₂—CH₂ | 2-Br—C₆H₄ | CH₃ | CH₃ | N—OCH₃ | |
| 162 | CH₂—CH₂ | 4-Br—C₆H₄ | CH₃ | CH₃ | N—OCH₃ | |
| 163 | CH₂—CH₂ | 2-I—C₆H₄ | CH₃ | CH₃ | N—OCH₃ | |
| 164 | CH₂—CH₂ | 2-CH₃—C₆H₄ | CH₃ | CH₃ | N—OCH₃ | |
| 165 | CH₂—CH₂ | 3-CH₃—C₆H₄ | CH₃ | CH₃ | N—OCH₃ | |
| 166 | CH₂—CH₂ | 4-CH₃—C₆H₄ | CH₃ | CH₃ | N—OCH₃ | |
| 167 | CH₂—CH₂ | 2-OCH₃—C₆H₄ | CH₃ | CH₃ | N—OCH₃ | |
| 168 | CH₂—CH₂ | 3-OCH₃—C₆H₄ | CH₃ | CH₃ | N—OCH₃ | |
| 169 | CH₂—CH₂ | 4-OCH₃—C₆H₄ | CH₃ | CH₃ | N—OCH₃ | |
| 170 | CH₂—CH₂ | 2-CF₃—C₆H₄ | CH₃ | CH₃ | N—OCH₃ | |
| 171 | CH₂—CH₂ | 3-CF₃—C₆H₄ | CH₃ | CH₃ | N—OCH₃ | |
| 172 | CH₂—CH₂ | 4-CF₃—C₆H₄ | CH₃ | CH₃ | N—OCH₃ | |
| 173 | CH₂—CH₂ | 2,4-Cl₂—C₆H₃ | CH₃ | CH₃ | N—OCH₃ | |
| 174 | CH₂—CH₂ | 2,4-(CH₃)₂—C₆H₃ | CH₃ | CH₃ | N—OCH₃ | |
| 175 | CH₂—CH₂ | 2,4,6-(CH₃)₃—C₆H₂ | CH₃ | CH₃ | N—OCH₃ | |
| 176 | CH₂—CH₂ | Pyridin-3-yl | CH₃ | CH₃ | N—OCH₃ | |
| 177 | CH₂—CH₂ | Furan-2-yl | CH₃ | CH₃ | N—OCH₃ | |
| 178 | CH₂—CH₂ | 6-CH₃-Pyridin-2-yl | CH₃ | CH₃ | N—OCH₃ | |
| 179 | CH₂—CH₂ | Benzothiazol-2-yl | CH₃ | CH₃ | N—OCH₃ | |
| 180 | CH=CH | C₆H₅ | CH₃ | CH₃ | N—OCH₃ | |
| 181 | CH=CH | 2-F—C₆H₄ | CH₃ | CH₃ | N—OCH₃ | |
| 182 | CH=CH | 3-F—C₆H₄ | CH₃ | CH₃ | N—OCH₃ | |
| 183 | CH=CH | 4-F—C₆H₄ | CH₃ | CH₃ | N—OCH₃ | |
| 184 | CH=CH | 2-Cl—C₆H₄ | CH₃ | CH₃ | N—OCH₃ | |
| 185 | CH=CH | 3-Cl—C₆H₄ | CH₃ | CH₃ | N—OCH₃ | |
| 186 | CH=CH | 4-Cl—C₆H₄ | CH₃ | CH₃ | N—OCH₃ | |
| 187 | CH=CH | 2-Br—C₆H₄ | CH₃ | CH₃ | N—OCH₃ | |
| 188 | CH=CH | 4-Br—C₆H₄ | CH₃ | CH₃ | N—OCH₃ | |
| 189 | CH=CH | 2-I—C₆H₄ | CH₃ | CH₃ | N—OCH₃ | |
| 190 | CH=CH | 2-CH₃—C₆H₄ | CH₃ | CH₃ | N—OCH₃ | |
| 191 | CH=CH | 3-CH₃—C₆H₄ | CH₃ | CH₃ | N—OCH₃ | |
| 192 | CH=CH | 4-CH₃—C₆H₄ | CH₃ | CH₃ | N—OCH₃ | |
| 193 | CH=CH | 2-OCH₃—C₆H₄ | CH₃ | CH₃ | N—OCH₃ | |
| 194 | CH=CH | 3-OCH₃—C₆H₄ | CH₃ | CH₃ | N—OCH₃ | |
| 195 | CH=CH | 4-OCH₃—C₆H₄ | CH₃ | CH₃ | N—OCH₃ | |
| 196 | CH=CH | 2-CF₃—C₆H₄ | CH₃ | CH₃ | N—OCH₃ | |
| 197 | CH=CH | 3-CF₃—C₆H₄ | CH₃ | CH₃ | N—OCH₃ | |
| 198 | CH=CH | 4-CF₃—C₆H₄ | CH₃ | CH₃ | N—OCH₃ | |

TABLE-continued (R² , R³ = H)

| No. | Y | R¹ | R⁴ | R⁵ | W | Physical data |
|---|---|---|---|---|---|---|
| 199 | CH=CH | 2,4-Cl₂—C₆H₃ | CH₃ | CH₃ | N—OCH₃ | |
| 200 | CH=CH | 2,4-(CH₃)₂—C₆H₃ | CH₃ | CH₃ | N—OCH₃ | |
| 201 | CH=CH | 2,4,6-(CH₃)₃—C₆H₂ | CH₃ | CH₃ | N—OCH₃ | |
| 202 | CH=CH | Pyridin-3-yl | CH₃ | CH₃ | N—OCH₃ | |
| 203 | CH=CH | Furan-2-yl | CH₃ | CH₃ | N—OCH₃ | |
| 204 | CH=CH | 6-CH₃-pyridin-2-yl | CH₃ | CH₃ | N—OCH₃ | |
| 205 | CH=CH | Benzothiazol-2-yl | CH₃ | CH₃ | N—OCH₃ | |
| 206 | CH₂O | C₆H₅ | CH₃ | CH₃ | N—OCH₃ | |
| 207 | CH₂O | 2-F—C₆H₄ | CH₃ | CH₃ | N—OCH₃ | |
| 208 | CH₂O | 3-F—C₆H₄ | CH₃ | CH₃ | N—OCH₃ | |
| 209 | CH₂O | 4-F—C₆H₄ | CH₃ | CH₃ | N—OCH₃ | |
| 210 | CH₂O | 2-Cl—C₆H₄ | CH₃ | CH₃ | N—OCH₃ | |
| 211 | CH₂O | 3-Cl—C₆H₄ | CH₃ | CH₃ | N—OCH₃ | |
| 212 | CH₂O | 4-Cl—C₆H₄ | CH₃ | CH₃ | N—OCH₃ | |
| 213 | CH₂O | 2-Br—C₆H₄ | CH₃ | CH₃ | N—OCH₃ | |
| 214 | CH₂O | 4-Br—C₆H₄ | CH₃ | CH₃ | N—OCH₃ | |
| 215 | CH₂O | 2-I—C₆H₄ | CH₃ | CH₃ | N—OCH₃ | |
| 216 | CH₂O | 2-CH₃—C₆H₄ | CH₃ | CH₃ | N—OCH₃ | |
| 217 | CH₂O | 3-CH₃—C₆H₄ | CH₃ | CH₃ | N—OCH₃ | |
| 218 | CH₂O | 4-CH₃—C₆H₄ | CH₃ | CH₃ | N—OCH₃ | |
| 219 | CH₂O | 2-OCH₃—C₆H₄ | CH₃ | CH₃ | N—OCH₃ | |
| 220 | CH₂O | 3-OCH₃—C₆H₄ | CH₃ | CH₃ | N—OCH₃ | |
| 221 | CH₂O | 4-OCH₃—C₆H₄ | CH₃ | CH₃ | N—OCH₃ | |
| 222 | CH₂O | 2-CF₃—C₆H₄ | CH₃ | CH₃ | N—OCH₃ | |
| 223 | CH₂O | 3-CF₃—C₆H₄ | CH₃ | CH₃ | N—OCH₃ | |
| 224 | CH₂O | 4-CF₃—C₆H₄ | CH₃ | CH₃ | N—OCH₃ | |
| 225 | CH₂O | 2,4-Cl₂—C₆H₃ | CH₃ | CH₃ | N—OCH₃ | |
| 226 | CH₂O | 2,4-(CH₃)₂—C₆H₃ | CH₃ | CH₃ | N—OCH₃ | |
| 227 | CH₂O | 2,4,6-(CH₃)₃—C₆H₂ | CH₃ | CH₃ | N—OCH₃ | |
| 228 | CH₂O | Pyridin-3-yl | CH₃ | CH₃ | N—OCH₃ | |
| 229 | CH₂O | Furan-2-yl | CH₃ | CH₃ | N—OCH₃ | |
| 230 | CH₂O | 6-CH₃-Pyridin-2-yl | CH₃ | CH₃ | N—OCH₃ | |
| 231 | CH₂O | Benzothiazol-2-yl | CH₃ | CH₃ | N—OCH₃ | |
| 232 | OCH₂ | C₆H₅ | CH₃ | CH₃ | N—OCH₃ | |
| 233 | OCH₂ | 2-F—C₆H₄ | CH₃ | CH₃ | N—OCH₃ | |
| 234 | OCH₂ | 3-F—C₆H₄ | CH₃ | CH₃ | N—OCH₃ | |
| 235 | OCH₂ | 4-F—C₆H₄ | CH₃ | CH₃ | N—OCH₃ | |
| 236 | OCH₂ | 2-Cl—C₆H₄ | CH₃ | CH₃ | N—OCH₃ | |
| 237 | OCH₂ | 3-Cl—C₆H₄ | CH₃ | CH₃ | N—OCH₃ | |
| 238 | OCH₂ | 4-Cl—C₆H₄ | CH₃ | CH₃ | N—OCH₃ | |
| 239 | OCH₂ | 2-Br—C₆H₄ | CH₃ | CH₃ | N—OCH₃ | |

TABLE-continued

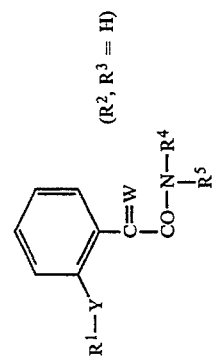

(R² , R³ = H)

| No. | Y | R¹ | R⁴ | R⁵ | W | Physical data |
|---|---|---|---|---|---|---|
| 240 | OCH₂ | 4-Br—C₆H₄ | CH₃ | CH₃ | N—OCH₃ | |
| 241 | OCH₂ | 2-I—C₆H₄ | CH₃ | CH₃ | N—OCH₃ | |
| 242 | OCH₂ | 2-CH₃—C₆H₄ | CH₃ | CH₃ | N—OCH₃ | M.p. 75° C., 1H-NMR(CDCl₃) 2.26(s, 3H); 3.02, 3.17(2s, 6H); 3.97(s, 3H); 5.17(s, 2H); 6.85 (m, 2H); 7.15(m, 2H); 7.40(m, 3H); 7.60(d, 1H) |
| 243 | OCH₂ | 3-CH₃—C₆H₄ | CH₃ | CH₃ | N—OCH₃ | |
| 244 | OCH₂ | 4-CH₃—C₆H₄ | CH₃ | CH₃ | N—OCH₃ | |
| 245 | OCH₂ | 2-OCH₃—C₆H₄ | CH₃ | CH₃ | N—OCH₃ | |
| 246 | OCH₂ | 3-OCH₃—C₆H₄ | CH₃ | CH₃ | N—OCH₃ | |
| 247 | OCH₂ | 4-OCH₃—C₆H₄ | CH₃ | CH₃ | N—OCH₃ | |
| 248 | OCH₂ | 2-CF₃—C₆H₄ | CH₃ | CH₃ | N—OCH₃ | |
| 249 | OCH₂ | 3-CF₃—C₆H₄ | CH₃ | CH₃ | N—OCH₃ | |
| 250 | OCH₂ | 4-CF₃—C₆H₄ | CH₃ | CH₃ | N—OCH₃ | |
| 251 | OCH₂ | 2,4-Cl₂—C₆H₃ | CH₃ | CH₃ | N—OCH₃ | |
| 252 | OCH₂ | 2,4-(CH₃)₂—C₆H₃ | CH₃ | CH₃ | N—OCH₃ | oil; 1H-NMR(CDCl₃); δ = 2.23(s, 3H); 2.27(s, 3H); 3.03, 3.18(2s, 6H); 3.93(s, 3H); 5.02(s, 2H); 6.75 (d, 1H); 6.9(m, 2H); 7.35(m, 3H); 7.57(d, 1H) |
| 253 | OCH₂ | 2,4,6-(CH₃)₃—C₆H₂ | CH₃ | CH₃ | N—OCH₃ | |
| 254 | OCH₂ | 2-CH₃, 4-Cl—C₆H₃ | CH₃ | CH₃ | N—OCH₃ | |
| 255 | OCH₂ | 3-t-C₄H₉—C₆H₄ | CH₃ | CH₃ | N—OCH₃ | |
| 256 | OCH₂ | 2-Cl, 4-CH₃—C₆H₃ | CH₃ | CH₃ | N—OCH₃ | |
| 257 | OCH₂ | 4-C₆H₅—C₆H₄ | CH₃ | CH₃ | N—OCH₃ | |
| 258 | OCH₂ | Pyridin-2-yl | CH₃ | CH₃ | N—OCH₃ | |
| 259 | OCH₂ | 6-CH₃-Pyridin-2-yl | CH₃ | CH₃ | N—OCH₃ | |
| 260 | OCH₂ | 6-Cl—Pyridin-2-yl | CH₃ | CH₃ | N—OCH₃ | |
| 261 | OCH₂ | Benzothiazol-2-yl | CH₃ | CH₃ | N—OCH₃ | |
| 262 | O | H | CH₃ | CH₃ | N—OCH₃ | |
| 263 | O | C₆H₅ | CH₃ | CH₃ | N—OCH₃ | |
| 264 | O | 3-C₆H₅—C₆H₄ | CH₃ | CH₃ | N—OCH₃ | |
| 265 | O | 3-n-C₃H₇—O—C₆H₄ | CH₃ | CH₃ | N—OCH₃ | |
| 266 | O | Pyridin-2-yl | CH₃ | CH₃ | N—OCH₃ | |
| 267 | O | 6-C₆H₅-Pyridin-2-yl | CH₃ | CH₃ | N—OCH₃ | |
| 268 | O | CH₂—CH=CH₂ | CH₃ | CH₃ | N—OCH₃ | |
| 269 | O | 3-C₆H₅O—C₆H₄ | CH₃ | CH₃ | N—OCH₃ | |
| 270 | O | 3-C₆H₅S—C₆H₄ | CH₃ | CH₃ | N—OCH₃ | |
| 271 | O | 3-C₆H₅CH₂O—C₆H₄ | CH₃ | CH₃ | N—OCH₃ | |
| 272 | C≡C | CH₃ | CH₃ | CH₃ | N—OCH₃ | |
| 273 | C≡C | C₆H₅ | CH₃ | CH₃ | N—OCH₃ | |
| 274 | S | C₆H₅ | CH₃ | CH₃ | N—OCH₃ | |
| 275 | S | 2-Cl—C₆H₄ | CH₃ | CH₃ | N—OCH₃ | |
| 276 | S—CH₂ | C₆H₅ | CH₃ | CH₃ | N—OCH₃ | |

TABLE-continued (R² , R³ = H)

| No. | Y | R¹ | R⁴ | R⁵ | W | Physical data |
|---|---|---|---|---|---|---|
| 277 | S—CH₂ | 4-Cl—C₆H₄ | CH₃ | CH₃ | N—OCH₃ | |
| 278 | S—CH₂ | 4-CH₃—C₆H₄ | CH₃ | CH₃ | N—OCH₃ | |
| 279 | S—CH₂ | 2-CH₃-Pyridin-2-yl | CH₃ | CH₃ | N—OCH₃ | |
| 280 | S—CH₂ | 6-Cl—Pyridin-2-yl | CH₃ | CH₃ | N—OCH₃ | |
| 281 | S—CH₂ | Benzothiazol-2-yl | CH₃ | CH₃ | N—OCH₃ | |
| 282 | S—CH₂ | 5-Cl—Benzothiazol-2-yl | CH₃ | CH₃ | N—OCH₃ | |
| 283 | S—CH₂ | 6-Cl—Benzothiazol-2-yl | CH₃ | CH₃ | N—OCH₃ | |
| 284 | CO—O— | CH₃ | CH₃ | CH₃ | N—OCH₃ | |
| 285 | CO—O— | C₆H₅ | CH₃ | CH₃ | N—OCH₃ | |
| 286 | O—CO— | CH₃ | CH₃ | CH₃ | N—OCH₃ | |
| 287 | O—CO— | C₆H₅ | CH₃ | CH₃ | N—OCH₃ | |
| 288 | O—CO— | H | CH₃ | CH₃ | N—OCH₃ | |
| 289 | CO—CH₂ | H | CH₃ | CH₃ | N—OCH₃ | |
| 290 | CO—CH₂ | CH₃ | CH₃ | CH₃ | N—OCH₃ | |
| 291 | CO—CH₂ | C₆H₅ | CH₃ | CH₃ | N—OCH₃ | |
| 292 | CO—CH₂ | 2-CH₃—C₆H₄ | CH₃ | CH₃ | N—OCH₃ | |
| 293 | CO—CH₂ | 2,4-(CH₃)₂—C₆H₃ | CH₃ | CH₃ | N—OCH₃ | |
| 294 | CO—CH₂ | 2-Cl—C₆H₄ | CH₃ | CH₃ | N—OCH₃ | |
| 295 | CO—CH₂ | Pyridin-2-yl | CH₃ | CH₃ | N—OCH₃ | |
| 296 | CO—CH₂ | Furan-2-yl | CH₃ | CH₃ | N—OCH₃ | |
| 297 | CO—CH₂ | Benzothiazol-2-yl | CH₃ | CH₃ | N—OCH₃ | |
| 298 | CH₂—CO | H | CH₃ | CH₃ | N—OCH₃ | |
| 299 | CH₂—CO | C₆H₅ | CH₃ | CH₃ | N—OCH₃ | |
| 300 | N=N | C₆H₅ | CH₃ | CH₃ | N—OCH₃ | |
| 301 | CO—OCH₂ | CH₃ | CH₃ | CH₃ | N—OCH₃ | |
| 302 | CO—OCH₂ | tert.-C₄H₉ | CH₃ | CH₃ | N—OCH₃ | |
| 303 | CO—OCH₂ | 3-Heptyl | CH₃ | CH₃ | N—OCH₃ | |
| 304 | CO—OCH₂ | Cyclopropyl | CH₃ | CH₃ | N—OCH₃ | |
| 305 | CO—OCH₂ | 1-Methylcyclopropyl | CH₃ | CH₃ | N—OCH₃ | |
| 306 | CO—OCH₂ | 2-Methylcyclopropyl | CH₃ | CH₃ | N—OCH₃ | |
| 307 | CO—OCH₂ | 2,2-Dichlorocyclopropyl | CH₃ | CH₃ | N—OCH₃ | |
| 308 | CO—OCH₂ | 2,2-Dimethylcyclopropyl | CH₃ | CH₃ | N—OCH₃ | |
| 309 | CO—OCH₂ | 2,2-Dimethyl-3-(2,2-Dichlorovinyl)cyclopropyl | CH₃ | CH₃ | N—OCH₃ | |
| 310 | CO—OCH₂ | 2-Phenylcyclopropyl | CH₃ | CH₃ | N—OCH₃ | |
| 311 | CO—OCH₂ | 1-(2-Fluorophenyl)cyclopropyl | CH₃ | CH₃ | N—OCH₃ | |
| 312 | CO—OCH₂ | 1-(2-Chlorophenyl)cyclopropyl | CH₃ | CH₃ | N OCH₃ | |
| 313 | CO—OCH₂ | 1-(2,6-Difluorophenyl)cyclopropyl | CH₃ | CH₃ | N—OCH₃ | |
| 314 | CO—OCH₂ | 1-(2,4-Dichlorphenyl)cyclopropyl | CH₃ | CH₃ | N—OCH₃ | |

TABLE-continued $(R^2, R^3 = H)$

| No. | Y | R¹ | R⁴ | R⁵ | W | Physical data |
|---|---|---|---|---|---|---|
| 315 | CO—OCH₂ | 1-(4-Chlorphenyl)cyclopropyl | CH₃ | CH₃ | N—OCH₃ | |
| 316 | CO—OCH₂ | 1-(4-Methoxyphenyl)-cyclopropyl | CH₃ | CH₃ | N—OCH₃ | |
| 317 | CO—OCH₂ | 1-(2-Methylphenyl)cyclopropyl | CH₃ | CH₃ | N—OCH₃ | |
| 318 | CO—OCH₂ | 1-(4-Methylphenyl)cyclopropyl | CH₃ | CH₃ | N—OCH₃ | |
| 319 | CO—OCH₂ | 1-Benzylcyclopropyl | CH₃ | CH₃ | N—OCH₃ | |
| 320 | CO—OCH₂ | Phenyl | CH₃ | CH₃ | N—OCH₃ | |
| 321 | CO—OCH₂ | 4-Methylphenyl | CH₃ | CH₃ | N—OCH₃ | |
| 322 | CO—OCH₂ | 4-Chlorophenyl | CH₃ | CH₃ | N—OCH₃ | |
| 323 | CO—OCH₂ | 4-Fluorophenyl | CH₃ | CH₃ | N—OCH₃ | |
| 324 | CO—OCH₂ | 2-Heptyl | CH₃ | CH₃ | N—OCH₃ | |
| 325 | CO—OCH₂ | Propargyl | CH₃ | CH₃ | N—OCH₃ | |
| 326 | CO—OCH₂ | 1-Methylcyclohexyl | CH₃ | CH₃ | N—OCH₃ | |
| 327 | CO—OCH₂ | Cyclohexyl | CH₃ | CH₃ | N—OCH₃ | |
| 328 | OCH₂ | C₆H₅ | C₂H₅ | CH₃ | N—OCH₃ | |
| 329 | OCH₂ | C₆H₅ | C₂H₅ | C₂H₅ | N—OCH₃ | |
| 330 | OCH₂ | C₆H₅ | n-C₃H₇ | CH₃ | N—OCH₃ | |
| 331 | CH₂ | H | CH₃ | H | N—OCH₃ | |
| 332 | CHCl | H | CH₃ | H | N—OCH₃ | |
| 333 | CHBr | H | CH₃ | H | N—OCH₃ | |
| 334 | CHO | H | CH₃ | H | N—OCH₃ | |
| 335 | CH₂O | H | CH₃ | H | N—OCH₃ | |
| 336 | CH₂—O—SO₂ | CH₃ | CH₃ | H | N—OCH₃ | |
| 337 | CH₂—O—SO₂ | C₆H₄—CH₃ | CH₃ | H | N—OCH₃ | |
| 338 | CH₂CH₂ | C₆H₅ | CH₃ | H | N—OCH₃ | |
| 339 | CH₂CH₂ | 2-F—C₆H₄ | CH₃ | H | N—OCH₃ | |
| 340 | CH₂CH₂ | 3-F—C₆H₄ | CH₃ | H | N—OCH₃ | |
| 341 | CH₂CH₂ | 4-F—C₆H₄ | CH₃ | H | N—OCH₃ | |
| 342 | CH₂CH₂ | 2-Cl—C₆H₄ | CH₃ | H | N—OCH₃ | |
| 343 | CH₂CH₂ | 3-Cl—C₆H₄ | CH₃ | H | N—OCH₃ | |
| 344 | CH₂CH₂ | 4-Cl—C₆H₄ | CH₃ | H | N—OCH₃ | |
| 345 | CH₂CH₂ | 2-Br—C₆H₄ | CH₃ | H | N—OCH₃ | |
| 346 | CH₂CH₂ | 3-Br—C₆H₄ | CH₃ | H | N—OCH₃ | |
| 347 | CH₂CH₂ | 4-Br—C₆H₄ | CH₃ | H | N—OCH₃ | |
| 348 | CH₂CH₂ | 2-I—C₆H₄ | CH₃ | H | N—OCH₃ | |
| 349 | CH₂CH₂ | 2-CH₃—C₆H₄ | CH₃ | H | N—OCH₃ | |
| 350 | CH₂CH₂ | 3-CH₃—C₆H₄ | CH₃ | H | N—OCH₃ | |
| 351 | CH₂CH₂ | 4-CH₃—C₆H₄ | CH₃ | H | N—OCH₃ | |
| 352 | CH₂CH₂ | 2-OCH₃—C₆H₄ | CH₃ | H | N—OCH₃ | |
| 353 | CH₂CH₂ | 3-OCH₃—C₆H₄ | CH₃ | H | N—OCH₃ | CHD 64 |
| 354 | CH₂CH₂ | 4-OCH₃—C₆H₄ | CH₃ | H | N—OCH₃ | |
| 355 | CH₂CH₂ | 2-CF₃—C₆H₄ | CH₃ | H | N—OCH₃ | |

TABLE-continued $(R^2, R^3 = H)$

| No. | Y | R¹ | R⁴ | R⁵ | W | Physical data |
|---|---|---|---|---|---|---|
| 356 | CH₂CH₂ | 3-CF₃—C₆H₄ | CH₃ | H | N—OCH₃ | |
| 357 | CH₂CH₂ | 4-CF₃—C₆H₄ | CH₃ | H | N—OCH₃ | |
| 358 | CH₂CH₂ | 4-i-C₃H₇—C₆H₄ | CH₃ | H | N—OCH₃ | |
| 359 | CH₂CH₂ | 4-t-C₄H₉—C₆H₄ | CH₃ | H | N—OCH₃ | |
| 360 | CH₂CH₂ | 4-C₆H₅—C₆H₄ | CH₃ | H | N—OCH₃ | |
| 361 | CH₂CH₂ | 2,4-Cl₂—C₆H₃ | CH₃ | H | N—OCH₃ | |
| 362 | CH₂CH₂ | 2,4-(CH₃)₂—C₆H₃ | CH₃ | H | N—OCH₃ | |
| 363 | CH₂CH₂ | 2,4,6-(CH₃)₃—C₆H₂ | CH₃ | H | N—OCH₃ | |
| 364 | CH₂CH₂ | 2,4,6-Cl₃—C₆H₂ | CH₃ | H | N—OCH₃ | |
| 365 | CH₂CH₂ | Pyridin-2-yl | CH₃ | H | N—OCH₃ | |
| 366 | CH₂CH₂ | Pyridin-3-yl | CH₃ | H | N—OCH₃ | |
| 367 | CH₂CH₂ | Furan-2-yl | CH₃ | H | N—OCH₃ | |
| 368 | CH₂CH₂ | 6-CH₃-Pyridin-2-yl | CH₃ | H | N—OCH₃ | |
| 369 | CH₂CH₂ | 6-Cl—Pyridin-2-yl | CH₃ | H | N—OCH₃ | |
| 370 | CH₂CH₂ | Benzothiazol-2-yl | CH₃ | H | N—OCH₃ | |
| 371 | CH=CH | C₆H₅ | CH₃ | H | N—OCH₃ | |
| 372 | CH=CH | 2-F—C₆H₄ | CH₃ | H | N—OCH₃ | |
| 373 | CH=CH | 3-F—C₆H₄ | CH₃ | H | N—OCH₃ | |
| 374 | CH=CH | 4-F—C₆H₄ | CH₃ | H | N—OCH₃ | |
| 375 | CH=CH | 2-Cl—C₆H₄ | CH₃ | H | N—OCH₃ | |
| 376 | CH=CH | 3-Cl—C₆H₄ | CH₃ | H | N—OCH₃ | |
| 377 | CH=CH | 4-Cl—C₆H₄ | CH₃ | H | N—OCH₃ | |
| 378 | CH=CH | 2-Br—C₆H₄ | CH₃ | H | N—OCH₃ | |
| 379 | CH=CH | 3-Br—C₆H₄ | CH₃ | H | N—OCH₃ | |
| 380 | CH=CH | 4-Br—C₆H₄ | CH₃ | H | N—OCH₃ | |
| 381 | CH=CH | 2-I—C₆H₄ | CH₃ | H | N—OCH₃ | |
| 382 | CH=CH | 2-CH₃—C₆H₄ | CH₃ | H | N—OCH₃ | |
| 383 | CH=CH | 3-CH₃—C₆H₄ | CH₃ | H | N—OCH₃ | |
| 384 | CH=CH | 4-CH₃—C₆H₄ | CH₃ | H | N—OCH₃ | |
| 385 | CH=CH | 2-OCH₃—C₆H₄ | CH₃ | H | N—OCH₃ | |
| 386 | CH=CH | 3-OCH₃—C₆H₄ | CH₃ | H | N—OCH₃ | |
| 387 | CH=CH | 4-OCH₃—C₆H₄ | CH₃ | H | N—OCH₃ | |
| 388 | CH=CH | 2-CF₃—C₆H₄ | CH₃ | H | N—OCH₃ | |
| 389 | CH=CH | 3-CF₃—C₆H₄ | CH₃ | H | N—OCH₃ | |
| 390 | CH=CH | 4-CF₃—C₆H₄ | CH₃ | H | N—OCH₃ | |
| 391 | CH=CH | 4-i-C₃H₇—C₆H₄ | CH₃ | H | N—OCH₃ | |
| 392 | CH=CH | 4-t-C₄H₉—C₆H₄ | CH₃ | H | N—OCH₃ | |
| 393 | CH=CH | 4-C₆H₅—C₆H₄ | CH₃ | H | N—OCH₃ | |
| 394 | CH=CH | 2,4-Cl₂-C₆H₃ | CH₃ | H | N—OCH₃ | |
| 395 | CH=CH | 2,4-(CH₃)₂—C₆H₃ | CH₃ | H | N—OCH₃ | |
| 396 | CH=CH | 2,4,6-(CH₃)₃—C₆H₂ | CH₃ | H | N—OCH₃ | |

TABLE-continued (R², R³ = H)

| No. | Y | R¹ | R⁴ | R⁵ | W | Physical data |
|---|---|---|---|---|---|---|
| 397 | CH=CH | 2,4,6-Cl₃—C₆H₂ | CH₃ | H | N—OCH₃ | |
| 398 | CH=CH | Pyridin-2-yl | CH₃ | H | N—OCH₃ | |
| 399 | CH=CH | Pyridin-3-yl | CH₃ | H | N—OCH₃ | |
| 400 | CH=CH | Furan-2-yl | CH₃ | H | N—OCH₃ | |
| 401 | CH=CH | 6-CH₃-Pyridin-2-yl | CH₃ | H | N—OCH₃ | |
| 402 | CH=CH | 6-Cl-Pyridin-2-yl | CH₃ | H | N—OCH₃ | |
| 403 | CH=CH | Benzothiazol-2-yl | CH₃ | H | N—OCH₃ | |
| 404 | CH₂O | C₆H₅ | CH₃ | H | N—OCH₃ | |
| 405 | CH₂O | 2-F—C₆H₄ | CH₃ | H | N—OCH₃ | |
| 406 | CH₂O | 3-F—C₆H₄ | CH₃ | H | N—OCH₃ | |
| 407 | CH₂O | 4-F—C₆H₄ | CH₃ | H | N—OCH₃ | |
| 408 | CH₂O | 2-Cl—C₆H₄ | CH₃ | H | N—OCH₃ | |
| 409 | CH₂O | 3-Cl—C₆H₄ | CH₃ | H | N—OCH₃ | |
| 410 | CH₂O | 4-Cl—C₆H₄ | CH₃ | H | N—OCH₃ | |
| 411 | CH₂O | 2-Br—C₆H₄ | CH₃ | H | N—OCH₃ | |
| 412 | CH₂O | 3-Br—C₆H₄ | CH₃ | H | N—OCH₃ | |
| 413 | CH₂O | 4-Br—C₆H₄ | CH₃ | H | N—OCH₃ | |
| 414 | CH₂O | 2-I—C₆H₄ | CH₃ | H | N—OCH₃ | |
| 415 | CH₂O | 2-CH₃—C₆H₄ | CH₃ | H | N—OCH₃ | |
| 416 | CH₂O | 3-CH₃—C₆H₄ | CH₃ | H | N—OCH₃ | |
| 417 | CH₂O | 4-CH₃—C₆H₄ | CH₃ | H | N—OCH₃ | |
| 418 | CH₂O | 2-OCH₃—C₆H₄ | CH₃ | H | N—OCH₃ | |
| 419 | CH₂O | 3-OCH₃—C₆H₄ | CH₃ | H | N—OCH₃ | |
| 420 | CH₂O | 4-OCH₃—C₆H₄ | CH₃ | H | N—OCH₃ | |
| 421 | CH₂O | 2-CF₃—C₆H₄ | CH₃ | H | N—OCH₃ | |
| 422 | CH₂O | 3-CF₃—C₆H₄ | CH₃ | H | N—OCH₃ | |
| 423 | CH₂O | 4-CF₃—C₆H₄ | CH₃ | H | N—OCH₃ | |
| 424 | CH₂O | 4-i-C₃H₇—C₆H₄ | CH₃ | H | N—OCH₃ | |
| 425 | CH₂O | 4-t-C₄H₉—C₆H₄ | CH₃ | H | N—OCH₃ | |
| 426 | CH₂O | 4-C₆H₅—C₆H₄ | CH₃ | H | N—OCH₃ | |
| 427 | CH₂O | 2,4-Cl₂—C₆H₃ | CH₃ | H | N—OCH₃ | |
| 428 | CH₂O | 2,4-(CH₃)₂—C₆H₃ | CH₃ | H | N—OCH₃ | |
| 429 | CH₂O | 2,4,6-(CH₃)₃—C₆H₂ | CH₃ | H | N—OCH₃ | |
| 430 | CH₂O | 2,4,6-Cl₃—C₆H₂ | CH₃ | H | N—OCH₃ | |
| 431 | CH₂O | Pyridin-2-yl | CH₃ | H | N—OCH₃ | |
| 432 | CH₂O | Pyridin-3-yl | CH₃ | H | N—OCH₃ | |
| 433 | CH₂O | Furan-2-yl | CH₃ | H | N—OCH₃ | |
| 434 | CH₂O | 6-CH₃-Pyridin-2-yl | CH₃ | H | N—OCH₃ | |
| 435 | CH₂O | 6-Cl-Pyridin-2-yl | CH₃ | H | N—OCH₃ | |
| 436 | CH₂O | Benzothiazol-2-yl | CH₃ | H | N—OCH₃ | |
| 437 | OCH₂ | H | CH₃ | H | N—OCH₃ | |

TABLE-continued

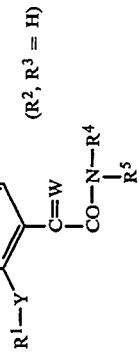

$R^1-Y$ (phenyl with) $C=W$, $CO-N-R^4$, $R^5$ ($R^2, R^3 = H$)

| No. | Y | R¹ | R⁴ | R⁵ | W | Physical data |
|-----|-----|-----|-----|-----|-----|-----|
| 438 | OCH₂ | C₆H₅ | CH₃ | H | N—OCH₃ | |
| 439 | OCH₂ | 2-F—C₆H₄ | CH₃ | H | N—OCH₃ | |
| 440 | OCH₂ | 3-F—C₆H₄ | CH₃ | H | N—OCH₃ | |
| 441 | OCH₂ | 4-F—C₆H₄ | CH₃ | H | N—OCH₃ | |
| 442 | OCH₂ | 2-Cl—C₆H₄ | CH₃ | H | N—OCH₃ | |
| 443 | OCH₂ | 3-Cl—C₆H₄ | CH₃ | H | N—OCH₃ | |
| 444 | OCH₂ | 4-Cl—C₆H₄ | CH₃ | H | N—OCH₃ | |
| 445 | OCH₂ | 2-Br—C₆H₄ | CH₃ | H | N—OCH₃ | |
| 446 | OCH₂ | 3-Br—C₆H₄ | CH₃ | H | N—OCH₃ | |
| 447 | OCH₂ | 4-Br—C₆H₄ | CH₃ | H | N—OCH₃ | |
| 448 | OCH₂ | 2-I—C₆H₄ | CH₃ | H | N—OCH₃ | |
| 449 | OCH₂ | 2-CH₃—C₆H₄ | CH₃ | H | N—OCH₃ | M.p. 105° C.; 1H-NMR(CDCl₃); δ=2.22(s, 3H); 2.85(d, 3H); 3.85(s, 3H); 4.95(s, 2H); 6.70(sbr, 1H); 6.80 (mc, 2H); 7.0–7.5(m, 6H) |
| 450 | OCH₂ | 3-CH₃—C₆H₄ | CH₃ | H | N—OCH₃ | |
| 451 | OCH₂ | 4-CH₃—C₆H₄ | CH₃ | H | N—OCH₃ | |
| 452 | OCH₂ | 2-OCH₃—C₆H₄ | CH₃ | H | N—OCH₃ | |
| 453 | OCH₂ | 3-OCH₃—C₆H₄ | CH₃ | H | N—OCH₃ | |
| 454 | OCH₂ | 4-OCH₃—C₆H₄ | CH₃ | H | N—OCH₃ | |
| 455 | OCH₂ | 2-CF₃—C₆H₄ | CH₃ | H | N—OCH₃ | |
| 456 | OCH₂ | 3-CF₃—C₆H₄ | CH₃ | H | N—OCH₃ | |
| 457 | OCH₂ | 4-CF₃—C₆H₄ | CH₃ | H | N—OCH₃ | |
| 458 | OCH₂ | 2-NO₂—C₆H₄ | CH₃ | H | N—OCH₃ | |
| 459 | OCH₂ | 4-NO₂—C₆H₄ | CH₃ | H | N—OCH₃ | |
| 460 | OCH₂ | 2-CH₂Cl—C₆H₄ | CH₃ | H | N—OCH₃ | |
| 461 | OCH₂ | 3-CH₂Cl—C₆H₄ | CH₃ | H | N—OCH₃ | |
| 462 | OCH₂ | 4-CH₂Cl—C₆H₄ | CH₃ | H | N—OCH₃ | |
| 463 | OCH₂ | 2-C₂H₅—C₆H₄ | CH₃ | H | N—OCH₃ | |
| 464 | OCH₂ | 3-C₂H₅—C₆H₄ | CH₃ | H | N—OCH₃ | |
| 465 | OCH₂ | 4-C₂H₅—C₆H₄ | CH₃ | H | N—OCH₃ | |
| 466 | OCH₂ | 3-i-C₃H₇—C₆H₄ | CH₃ | H | N—OCH₃ | |
| 467 | OCH₂ | 4-i-C₃H₇—C₆H₄ | CH₃ | H | N—OCH₃ | |
| 468 | OCH₂ | 3-t-C₄H₉—C₆H₄ | CH₃ | H | N—OCH₃ | |
| 469 | OCH₂ | 4-t-C₄H₉—C₆H₄ | CH₃ | H | N—OCH₃ | |
| 470 | OCH₂ | 3-C₆H₅—C₆H₄ | CH₃ | H | N—OCH₃ | |
| 471 | OCH₂ | 4-C₆H₅—C₆H₄ | CH₃ | H | N—OCH₃ | |
| 472 | OCH₂ | 4-i-C₃H₇O—C₆H₄ | CH₃ | H | N—OCH₃ | |
| 473 | OCH₂ | 4-t-C₄H₉O—C₆H₄ | CH₃ | H | N—OCH₃ | |
| 474 | OCH₂ | 3-C₆H₅O—C₆H₄ | CH₃ | H | N—OCH₃ | |
| 475 | OCH₂ | 4-C₆H₅O—C₆H₄ | CH₃ | H | N—OCH₃ | |
| 476 | OCH₂ | 3-C₆H₅CH₂O—C₆H₄ | CH₃ | H | N—OCH₃ | |

TABLE-continued $R^1-Y$ ... $C=W$, $CO-N-R^4$, $R^5$ ($R^2, R^3 = H$)

| No. | Y | R¹ | R⁴ | R⁵ | W | Physical data |
|---|---|---|---|---|---|---|
| 477 | OCH₂ | 4-C₆H₅CH₂O—C₆H₄ | CH₃ | H | N—OCH₃ | |
| 478 | OCH₂ | 2,3-Cl₂—C₆H₃ | CH₃ | H | N—OCH₃ | |
| 479 | OCH₂ | 2,4-Cl₂—C₆H₃ | CH₃ | H | N—OCH₃ | |
| 480 | OCH₂ | 2,5-Cl₂—C₆H₃ | CH₃ | H | N—OCH₃ | |
| 481 | OCH₂ | 2,6-Cl₂—C₆H₃ | CH₃ | H | N—OCH₃ | |
| 482 | OCH₂ | 2,3,4-Cl₃—C₆H₂ | CH₃ | H | N—OCH₃ | |
| 483 | OCH₂ | 2,3,5-Cl₃—C₆H₂ | CH₃ | H | N—OCH₃ | |
| 484 | OCH₂ | 2,4,5-Cl₃—C₆H₂ | CH₃ | H | N—OCH₃ | |
| 485 | OCH₂ | 2,3,6-Cl₃—C₆H₂ | CH₃ | H | N—OCH₃ | |
| 486 | OCH₂ | 3,4,5-Cl₃C₆H₂ | CH₃ | H | N—OCH₃ | |
| 487 | OCH₂ | C₆Cl₅ | CH₃ | H | N—OCH₃ | |
| 488 | OCH₂ | C₆F₅ | CH₃ | H | N—OCH₃ | |
| 489 | OCH₂ | 2-F, 4-Cl—C₆H₃ | CH₃ | H | N—OCH₃ | |
| 490 | OCH₂ | 4-F, 2-Cl—C₆H₃ | CH₃ | H | N—OCH₃ | |
| 491 | OCH₂ | 2-CH₃, 4-t-C₄H₉—C₆H₃ | CH₃ | H | N—OCH₃ | |
| 492 | OCH₂ | 2-CH₃, 4-c-C₆H₁₁—C₆H₃ | CH₃ | H | N—OCH₃ | |
| 493 | OCH₂ | 2-CH₃, 4-C₃H₇—C₆H₃ | CH₃ | H | N—OCH₃ | |
| 494 | OCH₂ | 2,3-(CH₃)₂—C₆H₃ | CH₃ | H | N—OCH₃ | M.p 88–89° C; IR(KBr): 3411, 1660, 1512, 1226, 1036, 982, 798, 766 |
| 495 | OCH₂ | 2,4-(CH₃)₂—C₆H₃ | CH₃ | H | N—OCH₃ | |
| 496 | OCH₂ | 2,5-(CH₃)₂—C₆H₃ | CH₃ | H | N—OCH₃ | |
| 497 | OCH₂ | 2,3,5-(CH₃)₃—C₆H₂ | CH₃ | H | N—OCH₃ | |
| 498 | OCH₂ | 2,4,6-(CH₃)₃—C₆H₂ | CH₃ | H | N—OCH₃ | |
| 499 | OCH₂ | 3,4-(CH₃)₂—C₆H₃ | CH₃ | H | N—OCH₃ | |
| 500 | OCH₂ | 3,5(CH₃)₂—C₆H₃ | CH₃ | H | N—OCH₃ | |
| 501 | OCH₂ | 3,5-(C₂H₅)₂—C₆H₃ | CH₃ | H | N—OCH₃ | |
| 502 | OCH₂ | 4-Cyclohexyl-C₆H₄ | CH₃ | H | N—OCH₃ | |
| 503 | OCH₂ | CH₂—CH=CH₂ | CH₃ | H | N—OCH₃ | |
| 504 | OCH₂ | CH₂—CH=CHCH₃ | CH₃ | H | N—OCH₃ | |
| 505 | OCH₂ | CH₂—CH=C(CH₃)₂ | CH₃ | H | N—OCH₃ | |
| 506 | OCH₂ | CH₂—C(CH₃)=CH₂ | CH₃ | H | N—OCH₃ | |
| 507 | OCH₂ | CH₂—C₆H₅ | CH₃ | H | N—OCH₃ | |
| 508 | OCH₂ | Cyclohexyl | CH₃ | H | N—OCH₃ | |
| 509 | OCH₂ | CH₂—C≡CH | CH₃ | H | N—OCH₃ | |
| 510 | OCH₂ | CH₂CH=CH—C₆H₅ | CH₃ | H | N—OCH₃ | |
| 511 | OCH₂ | CH₂CH₂—O—C₆H₅ | CH₃ | H | N—OCH₃ | |
| 512 | O | H | CH₃ | H | N—OCH₃ | |
| 513 | O | C₆H₅ | CH₃ | H | N—OCH₃ | |
| 514 | O | 3-C₆H₅—C₆H₄ | CH₃ | H | N—OCH₃ | |
| 515 | O | 3-n-C₃H₇O—C₆H₄ | CH₃ | H | N—OCH₃ | |
| 516 | O | Pyridin-2-yl | CH₃ | H | N—OCH₃ | |
| 517 | O | 6-C₆H₅-Pyridin-2-yl | CH₃ | H | N—OCH₃ | |

TABLE-continued

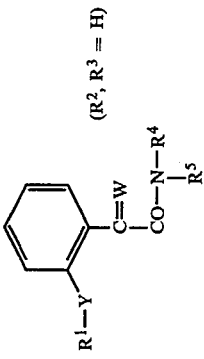

(R² , R³ = H)

| No. | Y | R¹ | R⁴ | R⁵ | W | Physical data |
|---|---|---|---|---|---|---|
| 517 | O | $CH_2-CH=CH_2$ | $CH_3$ | H | $N-OCH_3$ | |
| 518 | O | $3-C_6H_5O-C_6H_4$ | $CH_3$ | H | $N-OCH_3$ | |
| 519 | O | $3-C_6H_5-S-C_6H_4$ | $CH_3$ | H | $N-OCH_3$ | |
| 520 | O | $3-C_6H_5CH_2O-C_6H_4$ | $CH_3$ | H | $N-OCH_3$ | |
| 521 | O | $4-C_6H_5O-C_6H_4$ | $CH_3$ | H | $N-OCH_3$ | |
| 522 | O | $4-C_6H_5OCH_2-C_6H_4$ | $CH_3$ | H | $N-OCH_3$ | |
| 523 | C≡C | $CH_3$ | $CH_3$ | H | $N-OCH_3$ | |
| 524 | C≡C | $C_6H_5$ | $CH_3$ | H | $N-OCH_3$ | |
| 525 | S | $C_6H_5$ | $CH_3$ | H | $N-OCH_3$ | |
| 526 | S | $2-Cl-C_6H_4$ | $CH_3$ | H | $N-OCH_3$ | |
| 527 | $SCH_2$ | $C_6H_5$ | $CH_3$ | H | $N-OCH_3$ | |
| 528 | $SCH_2$ | $2-Cl-C_6H_4$ | $CH_3$ | H | $N-OCH_3$ | |
| 529 | $SCH_2$ | $4-Cl-C_6H_4$ | $CH_3$ | H | $N-OCH_3$ | |
| 530 | $SCH_2$ | $4-F-C_6H_4$ | $CH_3$ | H | $N-OCH_3$ | |
| 531 | $SCH_2$ | $4-CH_3-C_6H_4$ | $CH_3$ | H | $N-OCH_3$ | |
| 532 | $SCH_2$ | 4-$CH_3$-Pyridin-2-yl | $CH_3$ | H | $N-OCH_3$ | |
| 533 | $SCH_2$ | 6-Cl-Pyridin-2-yl | $CH_3$ | H | $N-OCH_3$ | |
| 534 | $SCH_2$ | Benzothiazol-2-yl | $CH_3$ | H | $N-OCH_3$ | |
| 535 | $SCH_2$ | 5-Cl-Benzothiazol-2-yl | $CH_3$ | H | $N-OCH_3$ | |
| 536 | $OCH_2$ | 6-Cl-Benzothiazol-2-yl | $CH_3$ | H | $N-OCH_3$ | |
| 537 | $OCH_2$ | 4,8-$(CH_3)_2$-Chinolin-2-yl | $CH_3$ | H | $N-OCH_3$ | |
| 538 | CO—O | $CH_3$ | $CH_3$ | H | $N-OCH_3$ | |
| 539 | CO—O | $C_6H_5$ | $CH_3$ | H | $N-OCH_3$ | |
| 540 | O—CO | $CH_3$ | $CH_3$ | H | $N-OCH_3$ | |
| 541 | O—CO | $C_6H_5$ | $CH_3$ | H | $N-OCH_3$ | |
| 542 | O—CO | $C_6H_5-CH_2$ | $CH_3$ | H | $N-OCH_3$ | |
| 543 | O—CO | H | $CH_3$ | H | $N-OCH_3$ | |
| 544 | $CO-CH_2$ | $CH_3$ | $CH_3$ | H | $N-OCH_3$ | |
| 545 | $CO-CH_2$ | $C_6H_5$ | $CH_3$ | H | $N-OCH_3$ | |
| 546 | $CO-CH_2$ | $2-CH_3-C_6H_4$ | $CH_3$ | H | $N-OCH_3$ | |
| 547 | $CO-CH_2$ | $2,4-(CH_3)_2-C_6H_3$ | $CH_3$ | H | $N-OCH_3$ | |
| 548 | $CO-CH_2$ | $2-Cl-C_6H_4$ | $CH_3$ | H | $N-OCH_3$ | |
| 549 | $CO-CH_2$ | H | $CH_3$ | H | $N-OCH_3$ | |
| 550 | $CH_2-CO$ | $C_6H_5$ | $CH_3$ | H | $N-OCH_3$ | |
| 551 | $CH_2-CO$ | $C_6H_5$ | $CH_3$ | H | $N-OCH_3$ | |
| 552 | N=N | $CH_3$ | $CH_3$ | H | $N-OCH_3$ | |
| 553 | $CO-OCH_2$ | tert.-$C_4H_9$ | $CH_3$ | H | $N-OCH_3$ | |
| 554 | $CO-OCH_2$ | 3-Heptyl | $CH_3$ | H | $N-OCH_3$ | |
| 555 | $CO-OCH_2$ | Cyclopropyl | $CH_3$ | H | $N-OCH_3$ | |
| 556 | $CO-OCH_2$ | 1-Methylcyclopropyl | $CH_3$ | H | $N-OCH_3$ | |
| 557 | $CO-OCH_2$ | | $CH_3$ | H | $N-OCH_3$ | |

TABLE-continued $R^1-Y-\underset{\underset{R^5}{|}}{\underset{CO-N-R^4}{C=W}}$  ($R^2$, $R^3$ = H)

| No. | Y | R¹ | R⁴ | R⁵ | W | Physical data |
|---|---|---|---|---|---|---|
| 558 | CO—OCH₂ | 2-Methylcyclopropyl | CH₃ | H | N—OCH₃ | |
| 559 | CO—OCH₂ | 2,2-Dimethylcyclopropyl | CH₃ | H | N—OCH₃ | |
| 560 | CO—OCH₂ | 2,2-Dichlorocyclopropyl | CH₃ | H | N—OCH₃ | |
| 561 | CO—OCH₂ | 2,2-Dimethyl-3-(2,2-Dichlorovinyl)cyclopropyl | CH₃ | H | N—OCH₃ | |
| 562 | CO—OCH₂ | 1-Phenylcyclopropyl | CH₃ | H | N—OCH₃ | |
| 563 | CO—OCH₂ | 1-(2-Fluorophenyl)cyclopropyl | CH₃ | H | N—OCH₃ | |
| 564 | CO—OCH₂ | 1-(2-Chlorophenyl)cyclopropyl | CH₃ | H | N OCH₃ | |
| 565 | CO—OCH₂ | 1-(2,6-Difluorophenyl)cyclopropyl | CH₃ | H | N—OCH₃ | |
| 566 | CO—OCH₂ | 1-(2,4-Dichlorophenyl)cyclopropyl | CH₃ | H | N—OCH₃ | |
| 567 | CO—OCH₂ | 1-(4-Chlorophenyl)cyclopropyl | CH₃ | H | N—OCH₃ | |
| 568 | CO—OCH₂ | 1-(4-Methoxyphenyl)cyclopropyl | CH₃ | H | N—OCH₃ | |
| 569 | CH₂ | H | C₂H₅ | H | N—OCH₃ | |
| 570 | CHCl | H | C₂H₅ | H | N—OCH₃ | |
| 571 | CHBr | H | C₂H₅ | H | N—OCH₃ | |
| 572 | CH=CH | C₆H₅ | C₂H₅ | H | N—OCH₃ | |
| 573 | CH=CH | C₆H₅ | C₂H₅ | H | N—OCH₃ | |
| 574 | OCH₂ | C₆H₅ | C₂H₅ | H | N—OCH₃ | |
| 575 | CH₂O | C₆H₅ | C₂H₅ | H | N—OCH₃ | |
| 576 | O | C₆H₅ | C₂H₅ | H | N—OCH₃ | |
| 577 | CH=CH | C₆H₅ | OCH₃ | H | N—OCH₃ | |
| 578 | CH₂ | H | OCH₃ | CH₃ | N—OCH₃ | |
| 579 | CHCl | H | OCH₃ | CH₃ | N—OCH₃ | |
| 580 | CHBr | H | OCH₃ | CH₃ | N—OCH₃ | |
| 581 | CH₂ | C₆H₅ | OCH₃ | H | N—OCH₃ | |
| 582 | OCH₂ | C₆H₅ | OCH₃ | H | N—OCH₃ | |
| 583 | OCH₂ | H | OC₂H₅ | H | N—OCH₃ | |
| 584 | OCH₂ | 2,4-(CH₃)₂—C₆H₃ | OCH₃ | H | N—OCH₃ | Oil; ¹H-NMR(CDCl₃); δ=2.24, 2.28(2s, 6H); 3.21(s, 3H); 3.52(br, 3H); 3.98(s, 3H); 5.05(s, 2H); 6.75 (d, 1H); 6.83(m, 2H); 7.40(mc, 3H); 7.64(d, 1H) |
| 585 | OCH₂ | 2-CH₃—C₆H₄ | OCH₃ | CH₃ | N—OCH₃ | M.p. 55° C.; ¹H-NMR(CDCl₃) δ=2.30(s, 3H); 3.20, 3.48(2s, 6H); 3.98(s, 3H); 5.08(s, 2H); 6.85(t, 2H); 7.10(m, 2H); 7.40(mc, 3H); 7.65(d, 1H) |
| 586 | OCH₂ | 2-CH₃—C₆H₄ | OCH₃ | CH₃ | N—OCH₃ | |
| 587 | OCH₂ | 2-CH₃—C₆H₄ | OCH₃ | H | N—OCH₃ | M.p. 89° C.; ¹H-NMR(CDCl₃) δ=2.22(s, 3H); 3.75 (s, 3H); 3.94(s, 3H); 4.98(s, 2H); 6.80(m, 2H); 7.13(m, 2H); 7.25(d, 1H); 7.40(mc, 2H); 7.55(d, 1H); 9.15(d, 1H) |
| 588 | OCH₂ | 2-CH₃—C₆H₄ | C₂H₅ | C₂H₅ | N—OCH₃ | oil; ¹H-NMR(CDCl₃) δ=1.18(t, 3H); 2.25(s, 3H); |

TABLE-continued

($R^2$, $R^3$ = H)

| No. | Y | $R^1$ | $R^4$ | $R^5$ | W | Physical data |
|---|---|---|---|---|---|---|
| 589 | $CH_2$ | H | $CH_3$ | H | $CH-OCH_3$ | 3.45(d, 3H); 3.93(s, 3H); 5.09(s, 2H); 6.85(m, 2H) 7.10(mc, 2H); 7.4(m, 3H); 7.60(d, 1H) |
| 590 | CHCl | H | $CH_3$ | H | $CH-OCH_3$ | |
| 591 | CHBr | H | $CH_3$ | H | $CH-OCH_3$ | |
| 592 | CHI | H | $CH_3$ | H | $CH-OCH_3$ | |
| 593 | $CH_2$ | OH | $CH_3$ | H | $CH-OCH_3$ | |
| 594 | $CH_2-O-SO_2$ | $CH_3$ | $CH_3$ | H | $CH-OCH_3$ | |
| 595 | $CH_2-O-SO_2$ | $C_6H_4-CH_3$ | $CH_3$ | H | $CH-OCH_3$ | |
| 596 | $CH_2-CH_2$ | $C_6H_5$ | $CH_3$ | H | $CH-OCH_3$ | |
| 597 | $CH_2-CH_2$ | $2-F-C_6H_4$ | $CH_3$ | H | $CH-OCH_3$ | |
| 598 | $CH_2-CH_2$ | $3-F-C_6H_4$ | $CH_3$ | H | $CH-OCH_3$ | |
| 599 | $CH_2-CH_2$ | $4-F-C_6H_4$ | $CH_3$ | H | $CH-OCH_3$ | |
| 600 | $CH_2-CH_2$ | $2-Cl-C_6H_4$ | $CH_3$ | H | $CH-OCH_3$ | |
| 601 | $CH_2-CH_2$ | $3-Cl-C_6H_4$ | $CH_3$ | H | $CH-OCH_3$ | |
| 602 | $CH_2-CH_2$ | $4-Cl-C_6H_4$ | $CH_3$ | H | $CH-OCH_3$ | |
| 603 | $CH_2-CH_2$ | $2-Br-C_6H_4$ | $CH_3$ | H | $CH-OCH_3$ | |
| 604 | $CH_2-CH_2$ | $3-Br-C_6H_4$ | $CH_3$ | H | $CH-OCH_3$ | |
| 605 | $CH_2-CH_2$ | $4-Br-C_6H_4$ | $CH_3$ | H | $CH-OCH_3$ | |
| 606 | $CH_2-CH_2$ | $2-I-C_6H_4$ | $CH_3$ | H | $CH-OCH_3$ | |
| 607 | $CH_2-CH_2$ | $2-CH_3-C_6H_4$ | $CH_3$ | H | $CH-OCH_3$ | |
| 608 | $CH_2-CH_2$ | $3-CH_3-C_6H_4$ | $CH_3$ | H | $CH-OCH_3$ | |
| 609 | $CH_2-CH_2$ | $4-CH_3-C_6H_4$ | $CH_3$ | H | $CH-OCH_3$ | |
| 610 | $CH_2-CH_2$ | $2-OCH_3-C_6H_4$ | $CH_3$ | H | $CH-OCH_3$ | |
| 611 | $CH_2-CH_2$ | $3-OCH_3-C_6H_4$ | $CH_3$ | H | $CH-OCH_3$ | |
| 612 | $CH_2-CH_2$ | $4-OCH_3-C_6H_4$ | $CH_3$ | H | $CH-OCH_3$ | |
| 613 | $CH_2-CH_2$ | $2-CF_3-C_6H_4$ | $CH_3$ | H | $CH-OCH_3$ | |
| 614 | $CH_2-CH_2$ | $3-CF_3-C_6H_4$ | $CH_3$ | H | $CH-OCH_3$ | |
| 615 | $CH_2-CH_2$ | $4-CF_3-C_6H_4$ | $CH_3$ | H | $CH-OCH_3$ | |
| 616 | $CH_2-CH_2$ | $4-i-C_3H_7-C_6H_4$ | $CH_3$ | H | $CH-OCH_3$ | |
| 617 | $CH_2-CH_2$ | $4-t-C_4H_9-C_6H_4$ | $CH_3$ | H | $CH-OCH_3$ | |
| 618 | $CH_2-CH_2$ | $4-C_6H_5-C_6H_4$ | $CH_3$ | H | $CH-OCH_3$ | |
| 619 | $CH_2-CH_2$ | $2,4-Cl_2-C_6H_3$ | $CH_3$ | H | $CH-OCH_3$ | |
| 620 | $CH_2-CH_2$ | $2,4-(CH_3)_4-C_6H_3$ | $CH_3$ | H | $CH-OCH_3$ | |
| 621 | $CH_2-CH_2$ | $2,4,6-(CH_3)_3-C_6H_2$ | $CH_3$ | H | $CH-OCH_3$ | |
| 622 | $CH_2-CH_2$ | $2,4,6-Cl_3-C_6H_2$ | $CH_3$ | H | $CH-OCH_3$ | |
| 623 | $CH_2-CH_2$ | Pyridin-2-yl | $CH_3$ | H | $CH-OCH_3$ | |
| 624 | $CH_2-CH_2$ | Pyridin-3-yl | $CH_3$ | H | $CH-OCH_3$ | |
| 625 | $CH_2-CH_2$ | Furan-2-yl | $CH_3$ | H | $CH-OCH_3$ | |
| 626 | $CH_2-CH_2$ | 6-$CH_3$-Pyridin-2-yl | $CH_3$ | H | $CH-OCH_3$ | |
| 627 | $CH_2-CH_2$ | 6-Cl-Pyridin-2-yl | $CH_3$ | H | $CH-OCH_3$ | |

TABLE-continued (R² , R³ = H)

| No. | Y | R¹ | R⁴ | R⁵ | W | Physical data |
|---|---|---|---|---|---|---|
| 628 | CH₂—CH₂ | Benzothiazol-2-yl | CH₃ | H | CH—OCH₃ | |
| 629 | CH=CH | C₆H₅ | CH₃ | H | CH—OCH₃ | |
| 630 | CH=CH | 2-F—C₆H₄ | CH₃ | H | CH—OCH₃ | |
| 631 | CH=CH | 3-F—C₆H₄ | CH₃ | H | CH—OCH₃ | |
| 632 | CH=CH | 4-F—C₆H₄ | CH₃ | H | CH—OCH₃ | |
| 633 | CH=cH | 2-Cl—C₆H₄ | CH₃ | H | CH=OCH₃ | |
| 634 | CH=CH | 3-Cl—C₆H₄ | CH₃ | H | CH—OCH₃ | |
| 635 | CH=CH | 4-Cl—C₆H₄ | CH₃ | H | CH—OCH₃ | |
| 636 | CH=CH | 2-Br—C₆H₄ | CH₃ | H | CH—OCH₃ | |
| 637 | CH=CH | 3-Br—C₆H₄ | CH₃ | H | CH—OCH₃ | |
| 638 | CH=CH | 4-Br—C₆H₄ | CH₃ | H | CH—OCH₃ | |
| 639 | CH=CH | 2-I—C₆H₄ | CH₃ | H | CH—OCH₃ | |
| 640 | CH=CH | 2-CH₃—C₆H₄ | CH₃ | H | CH—OCH₃ | |
| 641 | CH=CH | 3-CH₃—C₆H₄ | CH₃ | H | CH—OCH₃ | |
| 642 | CH=CH | 4-CH₃—C₆H₄ | CH₃ | H | CH—OCH₃ | |
| 643 | CH=CH | 2-OCH₃—C₆H₄ | CH₃ | H | CH—OCH₃ | |
| 644 | CH=CH | 3-OCH₃—C₆H₄ | CH₃ | H | CH—OCH₃ | |
| 645 | CH=CH | 4-OCH₃—C₆H₄ | CH₃ | H | CH—OCH₃ | |
| 646 | CH=CH | 2-CF₃—C₆H₄ | CH₃ | H | CH—OCH₃ | |
| 647 | CH=CH | 3-CF₃—C₆H₄ | CH₃ | H | CH—OCH₃ | |
| 648 | CH=CH | 4-CF₃=C₆H₄ | CH₃ | H | CH—OCH₃ | |
| 649 | CH=CH | 4-i-C₃H₇—C₆H₄ | CH₃ | H | CH—OCH₃ | |
| 650 | CH=CH | 4-t-C₄H₉—C₆H₄ | CH₃ | H | CH—OCH₃ | |
| 651 | CH=CH | 4-C₆H₅—C₆H₄ | CH₃ | H | CH—OCH₃ | |
| 652 | CH=CH | 2,4-Cl₂—C₆H₃ | CH₃ | H | CH—OCH₃ | |
| 653 | CH=CH | 2,4-(CH₃)₄—C₆H₃ | CH₃ | H | CH—OCH₃ | |
| 654 | CH=CH | 2,4,6-(CH₃)₃—C₆H₂ | CH₃ | H | CH—OCH₃ | |
| 655 | CH=CH | 2,4,6-Cl₃—C₆H₂ | CH₃ | H | CH—OCH₃ | |
| 656 | CH=CH | Pyridin-2-yl | CH₃ | H | CH—OCH₃ | |
| 657 | CH=CH | Pyridin-3-yl | CH₃ | H | CH—OCH₃ | |
| 658 | CH=CH | Furan-2-yl | CH₃ | H | CH—OCH₃ | |
| 659 | CH=CH | 6-CH₃-Pyridin-2-yl | CH₃ | H | CH—OCH₃ | |
| 660 | CH=CH | 6-Cl-Pyridin-2-yl | CH₃ | H | CH—OCH₃ | |
| 661 | CH=CH | Benzothiazol-2-yl | CH₃ | H | CH—OCH₃ | |
| 662 | CH₂O | C₆H₅ | CH₃ | H | CH—OCH₃ | |
| 663 | CH₂O | 2-F—C₆H₄ | CH₃ | H | CH—OCH₃ | |
| 664 | CH₂O | 3-F—C₆H₄ | CH₃ | H | CH—OCH₃ | |
| 665 | CH₂O | 4-F—C₆H₄ | CH₃ | H | CH—OCH₃ | |
| 666 | CH₂O | 2-Cl—C₆H₄ | CH₃ | H | CH—OCH₃ | |
| 667 | CH₂O | 3-Cl—C₆H₄ | CH₃ | H | CH—OCH₃ | |
| 668 | CH₂O | 4-Cl—C₆H₄ | CH₃ | H | CH—OCH₃ | |

TABLE-continued (R², R³ = H)

| No. | Y | R¹ | R⁴ | R⁵ | W | Physical data |
|---|---|---|---|---|---|---|
| 669 | CH₂O | 2-Br—C₆H₄ | CH₃ | H | CH—OCH₃ | |
| 670 | CH₂O | 3-Br—C₆H₄ | CH₃ | H | CH—OCH₃ | |
| 671 | CH₂O | 4-Br—C₆H₄ | CH₃ | H | CH—OCH₃ | |
| 672 | CH₂O | 2-I—C₆H₄ | CH₃ | H | CH—OCH₃ | |
| 673 | CH₂O | 2-CH₃—C₆H₄ | CH₃ | H | CH—OCH₃ | |
| 674 | CH₂O | 3-CH₃—C₆H₄ | CH₃ | H | CH—OCH₃ | |
| 675 | CH₂O | 4-CH₃—C₆H₄ | CH₃ | H | CH—OCH₃ | |
| 676 | CH₂O | 2-OCH₃—C₆H₄ | CH₃ | H | CH—OCH₃ | |
| 677 | CH₂O | 3-OCH₃—C₆H₄ | CH₃ | H | CH—OCH₃ | |
| 678 | CH₂O | 4-OCH₃—C₆H₄ | CH₃ | H | CH—OCH₃ | |
| 679 | CH₂O | 2-CF₃—C₆H₄ | CH₃ | H | CH—OCH₃ | |
| 680 | CH₂O | 3-CF₃—C₆H₄ | CH₃ | H | CH—OCH₃ | |
| 681 | CH₂O | 4-CF₃—C₆H₄ | CH₃ | H | CH—OCH₃ | |
| 682 | CH₂O | 4-i-C₃H₇—C₆H₄ | CH₃ | H | CH—OCH₃ | |
| 683 | CH₂O | 4-t-C₄H₉—C₆H₄ | CH₃ | H | CH—OCH₃ | |
| 684 | CH₂O | 4-C₆H₅—C₆H₄ | CH₃ | H | CH—OCH₃ | |
| 685 | CH₂O | 2,4-Cl₂—C₆H₃ | CH₃ | H | CH—OCH₃ | |
| 686 | CH₂O | 2,4-(CH₃)₄—C₆H₃ | CH₃ | H | CH—OCH₃ | |
| 687 | CH₂O | 2,4,6-(CH₃)₃—C₆H₂ | CH₃ | H | CH—OCH₃ | |
| 688 | CH₂O | 2,4,6-Cl₃—C₆H₂ | CH₃ | H | CH—OCH₃ | |
| 689 | CH₂O | Pyridin-2-yl | CH₃ | H | CH—OCH₃ | |
| 690 | CH₂O | Pyridin-3-yl | CH₃ | H | CH—OCH₃ | |
| 691 | CH₂O | Furan-2-yl | CH₃ | H | CH—OCH₃ | |
| 692 | CH₂O | 6-CH₃-Pyridin-2-yl | CH₃ | H | CH—OCH₃ | |
| 693 | CH₂O | 6-Cl-Pyridin-2-yl | CH₃ | H | CH—OCH₃ | |
| 694 | CH₂O | Benzothiazol-2-yl | CH₃ | H | CH—OCH₃ | |
| 695 | OCH₂ | H | CH₃ | H | CH—OCH₃ | |
| 696 | OCH₂ | C₆H₅ | CH₃ | H | CH—OCH₃ | |
| 697 | OCH₂ | 2-F—C₆H₄ | CH₃ | H | CH—OCH₃ | |
| 698 | OCH₂ | 3-F—C₆H₄ | CH₃ | H | CH—OCH₃ | |
| 699 | OCH₂ | 4-F—C₆H₄ | CH₃ | H | CH—OCH₃ | |
| 700 | OCH₂ | 2-Cl—C₆H₄ | CH₃ | H | CH—OCH₃ | |
| 701 | OCH₂ | 3-Cl—C₆H₄ | CH₃ | H | CH—OCH₃ | |
| 702 | OCH₂ | 4-Cl—C₆H₄ | CH₃ | H | CH—OCH₃ | |
| 703 | OCH₂ | 2-Br—C₆H₄ | CH₃ | H | CH—OCH₃ | |
| 704 | OCH₂ | 3-Br—C₆H₄ | CH₃ | H | CH—OCH₃ | |
| 705 | OCH₂ | 4-Br—C₆H₄ | CH₃ | H | CH—OCH₃ | |
| 706 | OCH₂ | 2-I—C₆H₄ | CH₃ | H | CH—OCH₃ | |
| 707 | OCH₂ | 2-CH₃—C₆H₄ | CH₃ | H | CH—OCH₃ | |
| 708 | OCH₂ | 3-CH₃—C₆H₄ | CH₃ | H | CH—OCH₃ | |
| 709 | OCH₂ | 4-CH₃—C₆H₄ | CH₃ | H | CH—OCH₃ | |

TABLE-continued ($R^2$, $R^3$ = H)

| No. | Y | R¹ | R⁴ | R⁵ | W | Physical data |
|---|---|---|---|---|---|---|
| 710 | OCH₂ | 2-OCH₃—C₆H₄ | CH₃ | H | CH—OCH₃ | |
| 711 | OCH₂ | 3-OCH₃—C₆H₄ | CH₃ | H | CH—OCH₃ | |
| 712 | OCH₂ | 4-OCH₃—C₆H₄ | CH₃ | H | CH—OCH₃ | |
| 713 | OCH₂ | 2-CF₃—C₆H₄ | CH₃ | H | CH—OCH₃ | |
| 714 | OCH₂ | 3-CF₃—C₆H₄ | CH₃ | H | CH—OCH₃ | |
| 715 | OCH₂ | 4-CF₃—C₆H₄ | CH₃ | H | CH—OCH₃ | |
| 716 | OCH₂ | 2-NO₂—C₆H₄ | CH₃ | H | CH—OCH₃ | |
| 717 | OCH₂ | 4-NO₂—C₆H₄ | CH₃ | H | CH—OCH₃ | |
| 718 | OCH₂ | 2-CH₂Cl—C₆H₄ | CH₃ | H | CH—OCH₃ | |
| 719 | OCH₂ | 3-CH₂Cl—C₆H₄ | CH₃ | H | CH—OCH₃ | |
| 720 | OCH₂ | 4-CH₂Cl—C₆H₄ | CH₃ | H | CH—OCH₃ | |
| 721 | OCH₂ | 2-C₂H₅—C₆H₄ | CH₃ | H | CH—OCH₃ | |
| 722 | OCH₂ | 3-C₂H₅—C₆H₄ | CH₃ | H | CH—OCH₃ | |
| 723 | OCH₂ | 4-C₂H₅—C₆H₄ | CH₃ | H | CH—OCH₃ | |
| 724 | OCH₂ | 3-i-C₃H₇—C₆H₄ | CH₃ | H | CH—OCH₃ | |
| 725 | OCH₂ | 4-i-C₃H₇—C₆H₄ | CH₃ | H | CH—OCH₃ | |
| 726 | OCH₂ | 3-t-C₄H₉—C₆H₄ | CH₃ | H | CH—OCH₃ | |
| 727 | OCH₂ | 4-t-C₄H₉—C₆H₄ | CH₃ | H | CH—OCH₃ | |
| 728 | OCH₂ | 3-C₆H₅—C₆H₄ | CH₃ | H | CH—OCH₃ | |
| 729 | OCH₂ | 4-C₆H₅—C₆H₄ | CH₃ | H | CH—OCH₃ | |
| 730 | OCH₂ | 4-i-C₃H₇O—C₆H₄ | CH₃ | H | CH—OCH₃ | |
| 731 | OCH₂ | 4-t-C₄H₉O—C₆H₄ | CH₃ | H | CH—OCH₃ | |
| 732 | OCH₂ | 3-C₆H₅O—C₆H₄ | CH₃ | H | CH—OCH₃ | |
| 733 | OCH₂ | 4-C₆H₅O—C₆H₄ | CH₃ | H | CH—OCH₃ | |
| 734 | OCH₂ | 3-C₆H₅CH₂O—C₆H₄ | CH₃ | H | CH—OCH₃ | |
| 735 | OCH₂ | 4-C₆H₅CH₂O—C₆H₄ | CH₃ | H | CH—OCH₃ | |
| 736 | OCH₂ | 2,3-Cl₂—C₆H₃ | CH₃ | H | CH—OCH₃ | |
| 737 | OCH₂ | 2,4-Cl₂—C₆H₃ | CH₃ | H | CH—OCH₃ | |
| 738 | OCH₂ | 2,5-Cl₂—C₆H₃ | CH₃ | H | CH—OCH₃ | |
| 739 | OCH₂ | 2,6-Cl₂—C₆H₃ | CH₃ | H | CH—OCH₃ | |
| 740 | OCH₂ | 2,3,4-Cl₃—C₆H₂ | CH₃ | H | CH—OCH₃ | |
| 741 | OCH₂ | 2,3,5-Cl₃—C₆H₂ | CH₃ | H | CH—OCH₃ | |
| 742 | OCH₂ | 2,3,6-Cl₃—C₆H₂ | CH₃ | H | CH—OCH₃ | |
| 743 | OCH₂ | C₆Cl₅ | CH₃ | H | CH—OCH₃ | |
| 744 | OCH₂ | C₆F₅ | CH₃ | H | CH—OCH₃ | |
| 745 | OCH₂ | 2-F, 4-Cl—C₆H₃ | CH₃ | H | CH—OCH₃ | |
| 746 | OCH₂ | 4-F, 2-Cl—C₆H₃ | CH₃ | H | CH—OCH₃ | |
| 747 | OCH₂ | 2-CH₃, 4-t-C₄H₉—C₆H₃ | CH₃ | H | CH—OCH₃ | |
| 748 | OCH₂ | 2-CH₃, 4-Cyclohexyl-C₆H₃ | CH₃ | H | CH—OCH₃ | |
| 749 | OCH₂ | 2-CH₂, 4-i-C₃H₇, —C₆H₃ | CH₃ | H | CH—OCH₃ | |
| 750 | OCH₂ | 2,3-(CH₃)₂—C₆H₃ | CH₃ | H | CH—OCH₃ | |

TABLE-continued (R² , R³ = H)

| No. | Y | R¹ | R⁴ | R⁵ | W | Physical data |
|---|---|---|---|---|---|---|
| 761 | OCH₂ | 2,4-(CH₃)₂—C₆H₃ | CH₃ | H | CH—OCH₃ | |
| 762 | OCH₂ | 2,5-(CH₃)₂—C₆H₃ | CH₃ | H | CH—OCH₃ | |
| 763 | OCH₂ | 2,3,5-(CH₃)₃—C₆H₂ | CH₃ | H | CH—OCH₃ | |
| 764 | OCH₂ | 2,4,6-(CH₃)₃—C₆H₂ | CH₃ | H | CH—OCH₃ | |
| 765 | OCH₂ | 3,4-(CH₃)₂—C₆H₃ | CH₃ | H | CH—OCH₃ | |
| 766 | OCH₂ | 3,5-(CH₃)₂—C₆H₃ | CH₃ | H | CH—OCH₃ | |
| 767 | OCH₂ | 3,5-(C₂H₅)₂—C₆H₃ | CH₃ | H | CH—OCH₃ | |
| 768 | OCH₂ | 4-Cyclohexyl-C₆H₄ | CH₃ | H | CH—OCH₃ | |
| 769 | OCH₂ | CH₂CH=CH₂ | CH₃ | H | CH—OCH₃ | |
| 770 | OCH₂ | CH₂—CH=CHCH₃ | CH₃ | H | CH—OCH₃ | |
| 771 | OCH₂ | CH₂=CH=C(CH₃)₂ | CH₃ | H | CH—OCH₃ | |
| 772 | OCH₂ | CH₂—C(CH₃)=CH₂ | CH₃ | H | CH—OCH₃ | |
| 773 | OCH₂ | CH₂—C₆H₅ | CH₃ | H | CH—OCH₃ | |
| 774 | OCH₂ | Cyclohexyl | CH₃ | H | CH—OCH₃ | |
| 775 | OCH₂ | CH₂—C≡CH | CH₃ | H | CH—OCH₃ | |
| 776 | OCH₂ | CH₂CH=CH—C₆H₅ | CH₃ | H | CH—OCH₃ | |
| 777 | OCH₂ | CH₂CH₂—O—C₆H₅ | CH₃ | H | CH—OCH₃ | |
| 778 | O | H | CH₃ | H | CH—OCH₃ | |
| 779 | O | C₆H₅ | CH₃ | H | CH—OCH₃ | |
| 780 | O | 3-C₆H₅—C₆H₄ | CH₃ | H | CH—OCH₃ | |
| 781 | O | 3-n-C₃H₇O—C₆H₄ | CH₃ | H | CH—OCH₃ | |
| 782 | O | Pyridin-2-yl | CH₃ | H | CH—OCH₃ | |
| 783 | O | 6-C₆H₅-Pyridin-2-yl | CH₃ | H | CH—OCH₃ | |
| 784 | O | CH₂—CH=CH₂ | CH₃ | H | CH—OCH₃ | |
| 785 | O | 3-C₆H₅O—C₆H₄ | CH₃ | H | CH—OCH₃ | |
| 786 | O | 3-C₆H₅—S—C₆H₄ | CH₃ | H | CH—OCH₃ | |
| 787 | O | 3-C₆H₅—CH₂O—C₆H₄ | CH₃ | H | CH—OCH₃ | |
| 788 | O | 4-C₆H₅O—C₆H₄ | CH₃ | H | CH—OCH₃ | |
| 789 | O | 4-C₆H₅OCH₂—C₆H₄ | CH₃ | H | CH—OCH₃ | |
| 790 | C=C | CH₃ | CH₃ | H | CH—OCH₃ | |
| 791 | C=C | C₆H₅ | CH₃ | H | CH—OCH₃ | |
| 792 | S | C₆H₅ | CH₃ | H | CH—OCH₃ | |
| 793 | S | 2-Cl—C₆H₄ | CH₃ | H | CH—OCH₃ | |
| 794 | SCH₂ | C₆H₅ | CH₃ | H | CH—OCH₃ | |
| 795 | SCH₂ | 2-Cl—C₆H₄ | CH₃ | H | CH—OCH₃ | |
| 796 | SCH₂ | 4-Cl—C₆H₄ | CH₃ | H | CH—OCH₃ | |
| 797 | SCH₂ | 4-F—C₆H₄ | CH₃ | H | CH—OCH₃ | |
| 798 | SCH₂ | 4-CH₃—C₆H₄ | CH₃ | H | CH—OCH₃ | |
| 799 | SCH₂ | 6-CH₃-Pyridin-2-yl | CH₃ | H | CH—OCH₃ | |
| 800 | SCH₂ | 6-Cl-Pyridin-2-yl | CH₃ | H | CH—OCH₃ | |
| 801 | SCH₂ | Benzothiazol-2-yl | CH₃ | H | CH—OCH₃ | |

TABLE-continued (R² , R³ = H)

| No. | Y | R¹ | R⁴ | R⁵ | W | Physical data |
|---|---|---|---|---|---|---|
| 802 | SCH₂ | 5-Cl-Benzothiazol-2-yl | CH₃ | H | CH—OCH₃ | |
| 803 | SCH₂ | 6-Cl-Benzothiazol-2-yl | CH₃ | H | CH—OCH₃ | |
| 804 | SCH₂ | 4,8-(CH₃)₂-quinolin-2-yl | CH₃ | H | CH—OCH₃ | |
| 805 | CO—O | CH₃ | CH₃ | H | CH—OCH₃ | |
| 806 | CO—O | C₆H₅ | CH₃ | H | CH—OCH₃ | |
| 807 | O—CO | CH₃ | CH₃ | H | CH—OCH₃ | |
| 808 | O—CO | C₆H₅ | CH₃ | H | CH—OCH₃ | |
| 809 | O—CO | CH₂C₆H₅ | CH₃ | H | CH—OCH₃ | |
| 810 | O—CO | H | CH₃ | H | CH—OCH₃ | |
| 811 | CO—CH₂ | CH₃ | CH₃ | H | CH—OCH₃ | |
| 812 | CO—CH₂ | C₆H₅ | CH₃ | H | CH—OCH₃ | |
| 813 | CO—CH₂ | C₆H₅ | CH₃ | H | CH—OCH₃ | |
| 814 | CO—CH₂ | 2-CH₃—C₆H₄ | CH₃ | H | CH—OCH₃ | |
| 815 | CO—CH₂ | 2,4-(CH₃)₂—C₆H₃ | CH₃ | H | CH—OCH₃ | |
| 816 | CO—CH₂ | 2-Cl—C₆H₄ | CH₃ | H | CH—OCH₃ | |
| 817 | CH₂—CO | H | CH₃ | H | CH—OCH₃ | |
| 818 | CH₂—CO | C₆H₅ | CH₃ | H | CH—OCH₃ | |
| 819 | N=N | C₆H₅ | CH₃ | H | CH—OCH₃ | |
| 820 | CO—OCH₂ | CH₃ | CH₃ | H | CH—OCH₃ | |
| 821 | CO—OCH₂ | tert.-C₄H₉ | CH₃ | H | CH—OCH₃ | |
| 822 | CO—OCH₂ | 1-Methyl-cyclopropyl | CH₃ | H | CH—OCH₃ | |
| 823 | CO—OCH₂ | 2,2-Dichlorocyclopropyl | CH₃ | H | CH—OCH₃ | |
| 824 | CO—OCH₂ | 2-Phenylcyclopropyl | CH₃ | H | CH—OCH₃ | |
| 825 | CO—OCH₂ | 1-(2-Chlorophenyl)cyclopropyl | CH₃ | H | CH—OCH₃ | |
| 826 | CH₂ | H | C₂H₅ | H | CH—OCH₃ | |
| 827 | CHCl | H | C₂H₅ | H | CH—OCH₃ | |
| 828 | CHBr | H | C₂H₅ | H | CH—OCH₃ | |
| 829 | CH₂CH₂ | C₆H₅ | C₂H₅ | H | CH—OCH₃ | |
| 830 | CH=CH | C₆H₅ | C₂H₅ | H | CH—OCH₃ | |
| 831 | OCH₂ | C₆H₅ | C₂H₅ | H | CH—OCH₃ | |
| 832 | CH₂O | C₆H₅ | C₂H₅ | H | CH—OCH₃ | |
| 833 | O | C₆H₅ | C₂H₅ | H | CH—OCH₃ | |
| 834 | CH₂ | C₆H₅ | OCH₃ | H | CH—OCH₃ | |
| 835 | CH=CH | C₆H₅ | OCH₃ | H | CH—OCH₃ | |
| 836 | CH₂ | H | OCH₃ | H | CH—OCH₃ | |
| 837 | CHCl | H | OCH₃ | H | CH—OCH₃ | |
| 838 | CHBr | H | OCH₃ | H | CH—OCH₃ | |
| 839 | CH₂ | H | OCH₃ | CH₃ | CH—OCH₃ | |
| 840 | OCH₂ | C₆H₅ | OCH₃ | CH₃ | CH—OCH₃ | |
| 841 | OCH₂ | C₆H₅ | OC₂H₅ | H | CH—OCH₃ | |
| 842 | CH₂CH₂ | C₆H₅ | H | H | CH—OMe | |

TABLE-continued $(R^2, R^3 = H)$

| No. | Y | $R^1$ | $R^4$ | $R^5$ | W | Physical data |
|---|---|---|---|---|---|---|
| 843 | CH=CH | $C_6H_5$ | H | H | CH—OMe | |
| 844 | $CH_2$ | $C_6H_5$ | H | H | CH—OMe | |
| 845 | $OCH_2$ | $C_6H_5$ | H | H | CH—OMe | |
| 846 | O | $C_6H_5$ | H | H | CH—OMe | |
| 847 | C≡C | $C_6H_5$ | H | H | CH—OMe | |
| 848 | S | $C_6H_5$ | H | H | CH—OMe | |
| 849 | $SCH_2$ | $C_6H_5$ | H | H | CH—OMe | |
| 850 | CO—O | $C_6H_5$ | H | H | CH—OMe | |
| 851 | O—CO | $C_6H_5$ | H | H | CH—OMe | |
| 852 | CO—$CH_2$ | $C_6H_5$ | $CH_3$ | $CH_3$ | CH—OMe | |
| 853 | $CH_2$—CO | $C_6H_5$ | $CH_3$ | $CH_3$ | CH—OMe | |
| 854 | $CH_2CH_2$ | $C_6H_5$ | $CH_3$ | $CH_3$ | CH—OMe | |
| 855 | CH=CH | $C_6H_5$ | $CH_3$ | $CH_3$ | CH—OMe | |
| 856 | $CH_2$ | $C_6H_5$ | $CH_3$ | $CH_3$ | CH—OMe | |
| 857 | $OCH_2$ | $C_6H_5$ | $CH_3$ | $CH_3$ | CH—OMe | |
| 858 | O | $C_6H_5$ | $CH_3$ | $CH_3$ | CH—OMe | |
| 859 | C≡C | $C_6H_5$ | $C_2H_5$ | $CH_3$ | CH—OMe | |
| 860 | S | $C_6H_5$ | $C_3H_7$ | $CH_3$ | CH—OMe | |
| 861 | $SCH_2$ | $C_6H_5$ | H | H | CH—$SCH_3$ | |
| 862 | CO—O | $C_6H_5$ | H | H | CH—$SCH_3$ | |
| 863 | O—CO | $C_6H_5$ | H | H | CH—$SCH_3$ | |
| 864 | CO—$CH_2$ | $C_6H_5$ | H | H | CH—$SCH_3$ | |
| 865 | $CH_2$—CO | $C_6H_5$ | H | H | CH—$SCH_3$ | |
| 866 | $CH_2$ | $C_6H_5$ | H | H | CH—$SCH_3$ | |
| 867 | $OCH_2$ | $C_6H_5$ | H | H | CH—$SCH_3$ | |
| 868 | $CH_2CH_2$ | $C_6H_5$ | $CH_3$ | $CH_3$ | CH—$SCH_3$ | |
| 869 | CH=CH | $C_6H_5$ | $CH_3$ | $CH_3$ | CH—$SCH_3$ | |
| 870 | $CH_2O$ | $C_6H_5$ | $CH_3$ | $CH_3$ | CH—$SCH_3$ | |
| 871 | $OCH_2$ | $C_6H_5$ | $CH_3$ | $CH_3$ | CH—$SCH_3$ | |
| 872 | O | $C_6H_5$ | $CH_3$ | $CH_3$ | CH—$SCH_3$ | |
| 873 | CO—$CH_2$ | $C_6H_5$ | $CH_3$ | $CH_3$ | CH—$SCH_3$ | |
| 874 | CH=CH | $C_6H_5$ | $CH_3$ | $CH_3$ | CH—$SCH_3$ | |
| 875 | $CH_2O$ | $C_6H_5$ | $CH_3$ | $CH_3$ | CH—$SCH_3$ | |
| 876 | $OCH_2$ | $C_6H_5$ | $CH_3$ | $CH_3$ | CH—$SCH_3$ | |
| 877 | O | $C_6H_5$ | $CH_3$ | $CH_3$ | CH—$SCH_3$ | |
| 878 | $CH_2CH_2$ | $C_6H_5$ | $CH_3$ | H | CH—$SCH_3$ | |
| 879 | CH=CH | $C_6H_5$ | $CH_3$ | H | CH—$SCH_3$ | |
| 880 | $CH_2O$ | $C_6H_5$ | $CH_3$ | H | CH—$SCH_3$ | |
| 881 | $OCH_2$ | $C_6H_5$ | $CH_3$ | H | CH—$SCH_3$ | |
| 882 | O | $C_6H_5$ | $CH_3$ | H | CH—$SCH_3$ | |
| 883 | CO—$OCH_2$ | 1-Methylcyclopropyl | $CH_3$ | H | CH—$SCH_3$ | |

TABLE-continued $R^1-Y$-C$_6$H$_4$-C(=W)-CO-N(R$^4$)(R$^5$)  (R$^2$, R$^3$ = H)

| No. | Y | R$^1$ | R$^4$ | R$^5$ | W | Physical data |
|---|---|---|---|---|---|---|
| 884 | C≡C | C$_6$H$_5$ | CH$_3$ | H | CH—SCH$_3$ | |
| 885 | S | C$_6$H$_5$ | CH$_3$ | H | CH—SCH$_3$ | |
| 886 | S—CH$_2$ | C$_6$H$_5$ | CH$_3$ | H | CH—SCH$_3$ | |
| 887 | CO—O | C$_6$H$_5$ | CH$_3$ | H | CH—SCH$_3$ | |
| 888 | O—CO | C$_6$H$_5$ | CH$_3$ | H | CH—SCH$_3$ | |
| 889 | CO—CH$_2$ | C$_6$H$_5$ | CH$_3$ | H | CH—SCH$_3$ | |
| 890 | CH$_2$—CO | C$_6$H$_5$ | CH$_3$ | H | CH—SCH$_3$ | |
| 891 | O—CH$_2$ | C$_6$H$_5$ | OCH$_3$ | H | CH—SCH$_3$ | |
| 892 | O—CH$_2$ | C$_6$H$_5$ | OCH$_3$ | CH$_3$ | CH—SCH$_3$ | |

EXAMPLES OF USE

The comparison substance was

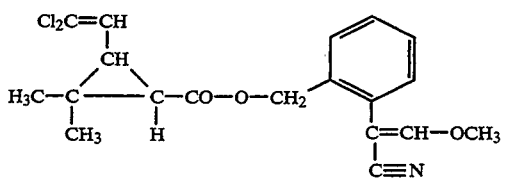

which is disclosed in EP-A 310 954 (compound No. 312; E/Z isomer mixture)

Example 5

Activity against Plasmopara viticola

Leaves of potted vines of the Müller-Thurgau variety were sprayed with 0,025% by weight aqueous suspensions containing 80% by weight active ingredient (Examples 87, 89, 93, 96,242, 252,449, 494, 585 and 586 in the table) and 20% by weight emulsifier in drymatter. To assess the duration of action after the sprayed-on layer had dried, the plants were placed in a greenhouse for 8 days. The leaves were then infected with a suspension of Plasmopara viticola spores and the plants were placed in a chamber saturated with water vapor at 24° C. for 48 hours. The vines were then grown in a greenhouse at from 20° to 30° C. for 5 days and, to accelerate sporangiophore for discharge, again placed in the humidity chamber for 16 hours. The extent of the fungus attack was then assessed on the undersides of the leaves.

Compared with a control test (no treatment, 60% fungus attack) and the known comparison compound A (35% fungus attack) it was found that the fungus attack was only from 0 to 5% on the plants treated with active ingredients 87, 89, 93, 96, 242, 252, 449, 494, 585 and 586.

Example 6

Activity against wheat mildew

Leaves of pot-grown wheat seedlings of the Frühgold variety were sprayed with 0.025% by weight aqueous formulations which contained 80% by weight active ingredient (Examples 449 and 587 in the table) and 20% by weight emulsifier in dry matter, and, 24 hours after the sprayed-on layer had dried, dusted with spores of wheat mildew (Erysiphe graminis var. tritici). The test plants were then placed in a greenhouse at from 20° to 22° C. and 75 to 80% relative humidity. The extent of mildew development was assessed after 7 days.

Compared with a control test (no treatment, 70% fungus attack) and the known comparison compound A (35% fungus attack) it was found that plants treated with active ingredients 449 and 587 had no fungus attack.

Example 7

Activity against Pyricularia oryzae (preventive treatment)

Leaves of pot-grown rice seedlings of the Bahia variety were sprayed to run off with aqueous emulsions which contained 80% active ingredient and 20% emulsifier in dry matter and, 24 hours later, infected with an aqueous suspension of Pyricularia oryzae spores. The test plants were then placed in chambers at from 20° to 24° C. and 95 to 99% relative humidity. The extent of fungus attack was determined after 6 days.

The result shows that active ingredients 242, 252, 449, 585 and 588 when used as 0.05% by weight aqueous formulation have a much better fungicidal action (93%) than the known comparison substance A (20%).

We claim:

1. A compound of the formula

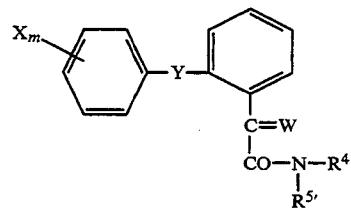

wherein $(X)_m$ is selected from the group consisting of:
- (a) one $C_1$-$C_4$-alkyl group; the saidd group being at position 2;
- (b) two independently selected $C_1$-$C_4$-alkyl groups, wherein at least one of the alkyl group; S at 2-position; and
- (c) three independently selected $C_1$-$C_4$-alkyl groups, wherein at least one of the alkyl group; S at 2-position;

Y is —OCH$_2$—

W is N—O$C_1$-$C_4$-alkyl; and each of $R^4$ and $R^5$ is independently selected from the group consisting of hydrogen and $C_1$-$C_4$-alkyl.

2. A fungicidal composition comprising a carrier and a fungicidally effective amount of a compound according to claim 1.

3. 2-Methoximino-2-[(2,4-dimethylphenoxymethyl)-phenyl]-acetic acid N-methylamide.

4. 2-Methoximino-2-[(2,5-dimethylphenoxymethyl)-phenyl]-acetic acid N-methylamide.

5. 2-Methoximino-2-[(2,3,5-trimethylphenoxymethyl)phenyl]-acetic acid N-methylamide.

6. 2-Methoximino-2-[(2-methylphenoxymethyl)-phenyl]-acetic acid N-methylamide.

* * * * *